US010251400B2

(12) United States Patent
Jabs et al.

(10) Patent No.: US 10,251,400 B2
(45) Date of Patent: Apr. 9, 2019

(54) **MIXTURES COMPRISING A *BACILLUS* STRAIN AND A PESTICIDE**

(71) Applicant: BASF SE, Ludwigshafen (DE)

(72) Inventors: Thorsten Jabs, Hassloch (DE); Nenad Filajdic, Raleigh, NC (US); Giridhar Ranuva, Morrisville, NC (US)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/313,229

(22) PCT Filed: May 13, 2015

(86) PCT No.: PCT/EP2015/060590
§ 371 (c)(1),
(2) Date: Nov. 22, 2016

(87) PCT Pub. No.: WO2015/177021
PCT Pub. Date: Nov. 26, 2015

(65) Prior Publication Data
US 2017/0188584 A1 Jul. 6, 2017

Related U.S. Application Data

(60) Provisional application No. 62/002,210, filed on May 23, 2014, provisional application No. 62/002,949, filed on May 26, 2014.

(30) Foreign Application Priority Data

Jul. 1, 2014 (EP) .................................... 14175139

(51) Int. Cl.
*A01N 63/00* (2006.01)
*A01N 47/24* (2006.01)
*A01N 43/56* (2006.01)
*A01N 25/00* (2006.01)
*A01N 63/02* (2006.01)
*A01N 37/50* (2006.01)
*A01N 43/40* (2006.01)
*A01N 43/54* (2006.01)
*A01N 43/80* (2006.01)
*A01N 47/02* (2006.01)
*A01N 47/12* (2006.01)
*A01N 51/00* (2006.01)
*A01N 43/653* (2006.01)

(52) U.S. Cl.
CPC ............ *A01N 63/00* (2013.01); *A01N 25/00* (2013.01); *A01N 63/02* (2013.01); *Y02A 50/356* (2018.01)

(58) Field of Classification Search
CPC combination set(s) only.
See application file for complete search history.

(56) References Cited

U.S. PATENT DOCUMENTS

| 5,215,747 | A | 6/1993 | Rosa |
| 5,501,852 | A | 3/1996 | Meadows et al. |
| 5,631,276 | A | 5/1997 | Kern |
| 5,747,025 | A | 5/1998 | Meadows et al. |
| 5,865,598 | A | 3/1999 | Knauf |
| 6,060,051 | A | 5/2000 | Orjala |
| 8,318,636 | B2 | 11/2012 | Alff |
| 8,445,255 | B2 | 5/2013 | Kloepper |
| 9,078,447 | B2 | 7/2015 | Haden |
| 2002/0152503 | A1 | 10/2002 | Purcell |
| 2003/0068303 | A1 | 4/2003 | Selvig |
| 2003/0224936 | A1 | 12/2003 | Kretzschmar |
| 2007/0244073 | A1 | 10/2007 | Angst et al. |
| 2010/0209410 | A1 | 8/2010 | Schoefl et al. |
| 2010/0260735 | A1 | 10/2010 | Kumar |
| 2011/0212835 | A1 | 9/2011 | Bais |
| 2012/0076765 | A1 | 3/2012 | Schisler |
| 2012/0094834 | A1 | 4/2012 | Frank |
| 2012/0149571 | A1 | 6/2012 | Kloepper |
| 2016/0278384 | A1 | 9/2016 | Seevers |

FOREIGN PATENT DOCUMENTS

| CL | 2012002419 | 7/2014 |
| CL | 2015002622 | 4/2016 |
| CN | 1086664 | 5/1994 |
| CN | 1335854 | 2/2002 |
| CN | 101028009 | 9/2007 |
| CN | 101697737 | 4/2010 |
| CN | 101917856 | 12/2010 |
| CN | 101697736 | 4/2012 |
| DE | 102009009240 | 8/2010 |
| EP | 1469122 | 10/2004 |
| EP | 1700919 | 9/2006 |
| GB | 2481118 | 12/2011 |
| RU | 2478290 C2 | 4/2013 |
| WO | 1994010846 | 5/1994 |
| WO | 1996019112 | 6/1996 |
| WO | 2000029426 | 5/2000 |
| WO | 2002060250 | 8/2002 |
| WO | 2002091824 | 11/2002 |
| WO | WO 2009037242 | 3/2009 |
| WO | 2010109436 | 9/2010 |
| WO | 2010128003 | 11/2010 |
| WO | 2010139656 | 12/2010 |
| WO | 2011117272 | 9/2011 |
| WO | WO11114280 A2 | 9/2011 |
| WO | WO 2011109395 | 9/2011 |
| WO | 2011147953 | 12/2011 |

(Continued)

OTHER PUBLICATIONS

Bartlett, D.W. et al., The strobilurin fungicides, Pest Management Science, vol. 58, pp. 649-662 (2002).*

(Continued)

*Primary Examiner* — John Pak
(74) *Attorney, Agent, or Firm* — Brinks Gilson & Lione

(57) ABSTRACT

The present invention relates to pesticidal mixtures comprising as active components the *Bacillus* strains AP-136, AP-188, APP-218, AP-219, AP-295, AP-209 and/or AP-217 as defined herein and a pesticide II as defined herein and respective agricultural uses thereof.

12 Claims, No Drawings

(56) References Cited

FOREIGN PATENT DOCUMENTS

| WO | | 2012047608 | 4/2012 |
|---|---|---|---|
| WO | | 2012072696 | 6/2012 |
| WO | | 2012076563 | 6/2012 |
| WO | | 2012080415 | 6/2012 |
| WO | WO 2012079073 | | 6/2012 |
| WO | WO 2014007663 | | 1/2014 |
| WO | WO 2014029697 | | 2/2014 |
| WO | | 2014053398 | 4/2014 |
| WO | WO 2014053398 | | 4/2014 |
| WO | | 2014076663 | 5/2014 |
| WO | | 2014079719 | 5/2014 |
| WO | | 2014079724 | 5/2014 |
| WO | | 2014079728 | 5/2014 |
| WO | | 2014079764 | 5/2014 |
| WO | | 2014079766 | 5/2014 |
| WO | | 2014079770 | 5/2014 |
| WO | | 2014079771 | 5/2014 |
| WO | | 2014079772 | 5/2014 |
| WO | | 2014079773 | 5/2014 |
| WO | | 2014079774 | 5/2014 |
| WO | | 2014079804 | 5/2014 |
| WO | | 2014079814 | 5/2014 |
| WO | | 2014079841 | 5/2014 |
| WO | WO 2014079804 | | 5/2014 |
| WO | WO 2014079814 | | 5/2014 |
| WO | WO 2014079841 | | 5/2014 |
| WO | | 2014086848 | 6/2014 |
| WO | | 2014086850 | 6/2014 |
| WO | | 2014086851 | 6/2014 |
| WO | | 2014086853 | 6/2014 |
| WO | | 2014086854 | 6/2014 |
| WO | | 2014086856 | 6/2014 |
| WO | WO 2014086856 | | 6/2014 |
| WO | | 2014147528 | 9/2014 |
| WO | | 2014147534 | 9/2014 |
| WO | WO 2014147528 | | 9/2014 |
| WO | WO 2014147534 | | 9/2014 |
| WO | WO 2015180983 | | 12/2015 |
| WO | WO 2015180985 | | 12/2015 |
| WO | WO 2015180987 | | 12/2015 |
| WO | WO 2015180999 | | 12/2015 |
| WO | WO 2015181008 | | 12/2015 |
| WO | WO 2015181009 | | 12/2015 |

OTHER PUBLICATIONS

Stamina supplemental label, BASF Corp., Research Triangle Park, NC, pp. 1-3 (2011).*

Facts on Friday bulletin, Cotton Seed Distributors Extension and Development Team, Jul. 23, 2010 (one page).*

Search Report, issued in EP Application No. 1475139.6, dated Dec. 18, 2014.

Final Office Action, issued in co-pending U.S. Appl. No. 14/777,850, dated Mar. 30, 2018.

Office Action, issued in co-pending U.S. Appl. No. 14/443,206, dated May 25, 2018.

Zitter et al. "Control of Early Blight of Tomato with Genetic Resistance and Conventional and Biological Sprays," Proc 1st IS on Tomato Diseases, Acta Hort, vol. 695, (2005), pp. 181-190.

Office Action, issued in co-pending U.S. Appl. No. 14/777,845. dated May 29, 2018.

Office Action, issued in CL Application No. 15/8002684, dated Mar. 27, 2017.

Office Action, issued in CN Application No. 201480016731.3, dated Apr. 28, 2017.

Wang, "Research Progress and Prospect of Bacillus Subtilis," Journal of the Graduates, Sun Yat-Sen University (Natural Sciences, Medicine), vol. 33, Issue 3, (2012), pp. 14-22.

Office Action, issued in co-pending U.S. Appl. No. 14/777,850, dated Mar. 24, 2017.

Schisler et al., "Formulation of Bacillus spp. for Biological Control of Plant Diseases," Journal of Phytopathology, vol. 94, (2004), pp. 1267-1271.

Office Action, issued in co-pending U.S. Appl. No. 14/777,845, dated Apr. 3, 2017.

Final Office Action, issued in co-pending U.S. Appl. No. 14/777,845, dated Nov. 22, 2017.

Final Office Action, issued in co-pending U.S. Appl. No. 14/443,206, dated Dec. 12, 2017.

Final Office Action, issued in co-pending U.S. Appl. No. 14/443,844, dated Jun. 23, 2017.

Office Action, issued in CN Application No. 201380071087.5, dated Apr. 26, 2017.

Office Action, issued in co-pending U.S. Appl. No. 14/443,206, dated Apr. 5, 2017.

Office Action, issued in UA Application No. 1506049, dated Feb. 14, 2017.

"Broadband," (Aug. 9, 2012), retrieved from Internet Jan. 29, 2014, url: http://beckerunderwood.com/media/products/resources/brouadband_instructions_B4D27D46613D6.pdf.

Office Action, issued in U.S. Appl. No. 14/443,523, dated Sep. 19, 2016.

Echeveeri-Molina et al., "Toxicity of Synthetic and Biological Insecticides against Adults of the Eucalyptus Snout-Beetle Gonipterus scutellatus Gyllenhall (Coleoptera: Curculionidae)," Journal of Pest Science, vol. 83, (2010), pp. 297-305.

Office Action, issued in co-pending U.S. Appl. No. 14/443,844, dated Feb. 14, 2017.

Singh et al., "DuPont Cyazypyr (TM) (DPX-HGW86, cyantraniliprole): A Cross-Spectrum Insecticide for Control of Major Pests of Rice," Abstract of Conference Paper, Entomological Society of America Annual, (2011), retrieved from the Internet on Feb. 9, 2017, url: https://www.researchgate.net/publication/267528306_DuPont_Cyazypyr_DPX-HGW86_c.

Leisso et al, "The Influence of Biological and Fungicidal Seed Treatment on Chickpea Damping Offi," Can. J. Plant Pathol., vol. 31, (2009), pp. 38-46.

Wright et al., "Application of Beneficial Microorganisms to Seeds during Drum Priming," Biocontrol Science and Technology, (2003), pp. 599-614.

Bennett et al., "Survival of the Biocontrol Agents Coniothyrium minitans and Bacillus subtillis MBI 600 Introduced into Pasturised, Sterilised and Non-Sterile Soils," Soil Biology & Biochemistry, vol. 35, (2003), pp. 1565-1573.

Schmidt et al., "Influence of Soil Temperature and Matric Potential on Sugar Beet Seedling Colonization and Suppression of Pythium Damping-Off by the Antagonistic Bacteria Pseudomonas fluorescens and Bacillus subtillis," Phytopathology, vol. 94, No. 4, (2004), pp. 351-363.

Zhang, "Evaluation of Microbial Products for Management of Powdery Mildew on Summer Squash and Cantaloupe in Florida," Plant Disease, (2011), pp. 461-468.

Zhou et al., "Field Evaluation of a Beneficial Bacillus strain for Biocontrol of Sheath Blight in Rice," Phytopathology, vol. 101, No. 6, Suppl. S, (2011), p. S204.

McKnight and Rossall, "Root Colonization of Cotton Seedlings by Bacillus subtilis MBI 600," 2nd International Workshop on Plant Growth-Promoting Rhizobacteria, (1991), pp. 365-369.

Enebak et al., "Evidence for Induced Systemic Protection to Fusiform Rust in Loblolly Pine by Plant Growth-Promoting Rhizobacteria," The American Phytopathological Society, Plant Disease, vol. 84, No. 3, (2000), pp. 306-308.

Farenhorst et al., "Synergy in Efficacy of Fungal Entomopathogens and Permethrin against West African Insecticide-Resistant Anopheles gambiae Mosquitoes," PloS One, vol. 5, Issue 8, (2010), pp. 1-10.

Koch et al., "Biosynthesis of cis-Jasmone: A Pathway for the Inactivation and the Disposal of the Plant Stress Hormone Jasmonic Acid to the Gas Phase?" Helvetica Chimica Acta, vol. 80, (1997), pp. 838-850.

Office Action, issued in co-pending U.S. Appl. No. 14/443,520, dated Oct. 14, 2016.

International Search Report, issued in PCT/EP2015/060590, dated Aug. 3, 2015.

(56) References Cited

OTHER PUBLICATIONS

International Preliminary Report on Patentability, issued in PCT/EP2015/060590, dated Nov. 29, 2016.

* cited by examiner

MIXTURES COMPRISING A *BACILLUS* STRAIN AND A PESTICIDE

This application is a National Stage application of International Application No. PCT/EP2015/060590, filed May 13, 2015, which claims the benefit of U.S. Provisional Application No. 62/002,210, filed May 23, 2014, and U.S. Provisional Application No. 62/002,949, filed May 26, 2014. This application also claims priority under 35 U.S.C. § 119 to European Patent Application No. 14175139.6, filed Jul. 1, 2014.

The present invention relates to mixtures comprising, as active components the *Bacillus* strains AP-136, AP-188, APP-218, AP-219, AP-295, AP-209 and/or AP-217 and a pesticide.

This microorganisms *Bacillus amyloliquefaciens* AP-136, AP-188, AP-218, AP-219, AP-295, *Bacillus mojavensis* AP-209 and *Bacillus solisalsi* AP-217 are known from US 2012/0149571, the content of which is incorporated by reference in its entirety. They have been described therein specifically as inoculants for promoting the plant defense response against herbivorous insects.

The strain *B. amyloliquefaciens* AP-136 has been deposited with the United States Department of Agriculture (USDA) on Nov. 5, 2009 under accession number (acc. no.) NRRL B-50330 and on Dec. 2, 2011 under acc. no. NRRL B-50614. The strain *B. amyloliquefaciens* AP-188 has been deposited with USDA on Nov. 5, 2009 under acc. no. NRRL B-50331 and on Dec. 2, 2011 under acc. no. NRRL B-50615. The strain *B. amyloliquefaciens* AP-218 has been deposited with USDA on Dec. 2, 2011 under acc. no. NRRL B-50618. The strain *B. amyloliquefaciens* AP-219 has been deposited with USDA on Nov. 5, 2009 under acc. no. NRRL B-50332 and on Dec. 2, 2011 under acc. no. NRRL B-50619. The strain *B. amyloliquefaciens* AP-295 has been deposited with USDA on Nov. 5, 2009 under acc. no. NRRL B-50333 and on Dec. 2, 2011 under acc. no. NRRL B-50620. The strain *B. mojavensis* AP-209 has been deposited with USDA on Dec. 2, 2011 under acc. no. NRRL B-50616. The strain *B. solisalsi* AP-217 has been deposited with USDA on Dec. 2, 2011 under acc. no. NRRL B-50617.

A pesticide is generally a chemical or biological agent (such as a virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease.

Biopesticides have been defined as a form of pesticides based on micro-organisms (bacteria, fungi, viruses, nematodes, etc.) or natural products (compounds, such as metabolites, proteins, or extracts from biological or other natural sources) (U.S. Environmental Protection Agency: http://www.epa.gov/pesticides/biopesticides/). Biopesticides fall into two major classes, microbial and biochemical pesticides:

(1) Microbial pesticides consist of bacteria, fungi or viruses (and often include the metabolites that bacteria and fungi produce).

(2) Biochemical pesticides are naturally occurring substances or or structurally-similar and functionally identical to a naturally-occurring substance and extracts from biological sources that control pests or provide other crop protection uses as defined below, but have non-toxic mode of actions and are relatively non-toxic to mammals.

Biopesticides for use against crop diseases have already established themselves on a variety of crops. For example, biopesticides already play an important role in controlling downy mildew diseases. Their benefits include: a 0-Day Pre-Harvest Interval, the ability to use under moderate to severe disease pressure, and the ability to use in mixture or in a rotational program with other registered pesticides.

However, biopesticides under certain conditions can also have disadvantages such as high specificity: which may require an exact identification of the pest/pathogen and the use of multiple products to be used, slow speed of action (thus making them unsuitable if a pest outbreak is an immediate threat to a crop), variable efficacy due to the influences of various biotic and abiotic factors (since biopesticides are usually living organisms, which bring about pest/pathogen control by multiplying within the target insect pest/pathogen) and resistance development.

Practical agricultural experience has shown that the repeated and exclusive application of an individual active component in the control of harmful fungi, insects or other pests leads in many cases to a rapid selection of those fungus strains or pest isolates which have developed natural or adapted resistance against the active component in question. Effective control of these fungi, insects or other pests with the active component in question is then no longer possible. Another typical problem arising in the field of pest control lies in the need to reduce the dosage rates of the active ingredient in order to reduce or avoid unfavorable environmental or toxicological effects whilst still allowing effective pest control.

It is an object of the present invention overcome the abovementioned disadvantages and to provide, with a view to effective resistance management and effective control of phytopathogenic harmful fungi, insects or other pests or to effective plant growth regulation, at application rates which are as low as possible, compositions which, at a reduced total amount of active compounds applied, have improved activity against the harmful fungi, insects or other pests or improved plant growth regulating activity (synergistic mixtures) and a broadened activity spectrum, in particular for certain indications.

This is particularly visible if application rates for the beforementioned mixtures of pesticides are used where the individual components show no or virtually no activity. The invention can also result in an advantageous behavior during formulation or during use, for example during grinding, sieving, emulsifying, dissolving or dispensing; improved storage stability and light stability, advantageous residue formation, improved toxicological or ecotoxicological behaviour, improved properties of the plant, for example better growth, increased harvest yields, a better developed root system, a larger leaf area, greener leaves, stronger shoots, less seed required, lower phytotoxicity, mobilization of the defense system of the plant, improved compatibility with plants.

It was therefore also an object of the present invention to provide pesticidal mixtures which solve the problems of reducing the dosage rate and/or enhancing the spectrum of activity and/or combining knock-down activity with prolonged control and/or to resistance management and/or promoting (increasing) the health of plants.

We have accordingly found that this object is achieved by the mixtures and compositions defined herein, comprising at least one microorganism of the genus *Bacillus* seleted from *B. amyloliquefaciens* AP-136 (NRRL B-50330; NRRL B-50614), *B. amyloliquefaciens* AP-188 (NRRL B-50331; NRRL B-50615), *B. amyloliquefaciens* AP-218 (NRRL B-50618), *B. amyloliquefaciens* AP-219 (NRRL B-50332, NRRL B-50619), *B. amyloliquefaciens* AP-295 (NRRL B-50333, NRRL B-50620) *B. mojavensis* AP-209 (NRRL B-50616), and *B. solisalsi* AP-217 (NRRL B-50617).

Thus, the present invention relates to mixtures comprising, as active components 1) at least one microorganism I of the genus *Bacillus* selected from:

*B. amyloliquefaciens* AP-136 (NRRL B-50330; NRRL B-50614),

*B. amyloliquefaciens* AP-188 (NRRL B-50331; NRRL B-50615),

*B. amyloliquefaciens* AP-218 (NRRL B-50618),

*B. amyloliquefaciens* AP-219 (NRRL B-50332, NRRL B-50619),

*B. amyloliquefaciens* AP-295 (NRRL B-50333, NRRL B-50620)

*B. mojavensis* AP-209 (NRRL B-50616), and

*B. solisalsi* AP-217 (NRRL B-50617);

and 2) at least one pesticide II from the groups A) to O) selected from:

A) Respiration inhibitors

Inhibitors of complex III at $Q_o$ site selected from: azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxystrobin (A.1.13), pyraclostrobin (A.1.14), pyrametostrobin (A.1.15), pyraoxystrobin (A.1.16), trifloxystrobin (A.1.17), 2-(2-(3-(2,6-dichlorophenyl)-1-methyl-allylideneaminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5-phenyl-pyrazol-3-yl)oxylmethyl]phenyl]N-methoxy-carbamate (A.1.22), 1-[3-chloro-2-[[[1-(4-chlorophenyl)-1H-pyrazol-3-yl]oxy]methyl]phenyl]-1,4-dihydro-4-methyl-5H-tetrazol-5-one (A.1.23), (2E,3Z)-5-[[1-(2,4-dichlorophenyl)-1H-pyrazol-3-yl]oxy]-2-(methoxyimino)-N,3-dimethyl-pent-3-enamide (A.1.24). (2E,3Z)-5-[[1-(4-chlorophenyl)-1H-pyrazol-3-yl]oxy]-2-(methoxyimino)-N,3-dimethyl-pent-3-enamide (A.1.25);

inhibitors of complex III at Q site selected from: cyazofamid (A.2.1), amisulbrom (A.2.2), [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate (A.2.3), [(3S,6S,7R,8R)-8-benzyl-3-[[3-(acet-oxymethoxy)-4-methoxy-pyridine-2-carbonyl]amino]-6-methyl-4,9-dioxo-1,5-dioxonan-7-yl] 2-methylpropanoate (A.2.4), [(3S,6S,7R,8R)-8-benzyl-3-[(3-isobutoxycarbonyloxy-4-meth-oxy-pyridine-2-carbonyl)amino]-6-methyl-4,9-dioxo-1,5-dioxonan-7-yl] 2-methylpropanoate (A.2.5), [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate (A.2.6); (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate (A.2.7);

inhibitors of complex II selected from: benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.14), penthiopyrad (A.3.15), sedaxane (A.3.16), tecloftalam (A.3.17), thifluzamide (A.3.18), N-(4'-trifluoromethylthiobiphenyl-2-yl)-3-difluoromethyl-1-methyl-1H-pyrazole-4-carboxamide (A.3.19), N-(2-(1,3,3-trimethyl-butyl)-phenyl)-1,3-dimethyl-5-fluoro-1H-pyrazole-4-carboxamide (A.3.20), 3-(difluoromethyl)-1-methyl-N-(1,1,3-trimethylindan-4-yl)pyrazole-4-carboxamide (A.3.21), 3-(trifluoromethyl)-1-methyl-N-(1,1,3-trimethylindan-4-yl)pyrazole-4-carboxamide (A.3.22), 1,3-dimethyl-N-(1,1,3-trimethylindan-4-yl)pyrazole-4-carboxamide (A.3.23), 3-(trifluoromethyl)-1,5-dimethyl-N-(1,1,3-trimethylindan-4-yl)pyrazole-4-carboxamide (A.3.24), 1,3,5-trimethyl-N-(1,1,3-trimethylindan-4-yl)pyrazole-4-carboxamide (A.3.25), N-(7-fluoro-1,1,3-trimethyl-indan-4-yl)-1,3-dimethyl-pyrazole-4-carboxamide (A.3.26), N-[2-(2,4-dichlorophenyl)-2-methoxy-1-methyl-ethyl]-3-(difluoromethyl)-1-methyl-pyrazole-4-carboxamide (A.3.27);

other respiration inhibitors selected from: diflumetorim (A.4.1), (5,8-difluoroquinazolin-4-yl)-{2-[2-fluoro-4-(4-trifluoromethylpyridin-2-yloxy)-phenyl]-ethyl}-amine(A.4.2); nitrophenyl derivates: binapacryl (A.4.3), dinobuton (A.4.4), dinocap (A.4.5), fluazinam (A.4.6); ferimzone (A.4.7); organometal compounds: fentin salts, such as fentin-acetate (A.4.8), fentin chloride (A.4.9) or fentin hydroxide (A.4.10); ametoctradin (A.4.11); and silthiofam (A.4.12);

B) Sterol biosynthesis inhibitors (SBI fungicides)

C14 demethylase inhibitors (DMI fungicides) selected from: triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 1-[rel-(2S;3R)-3-(2-chlorophenyl)-2-(2,4-difluorophenyl)-oxiranyl-methyl]-5-thiocyanato-1H-[1,2,4]triazolo (B.1.31), 2-[rel-(2S;3R)-3-(2-chlorophenyl)-2-(2,4-difluorophenyl)-oxiranylmethyl]-2H-[1,2,4]triazole-3-thiol (B.1.32), 2-[2-chloro-4-(4-chloro-phenoxy)phenyl]-1-(1,2,4-triazol-1-yl)pentan-2-ol (B.1.33), 1-[4-(4-chlorophenoxy)-2-(tri-fluoromethyl)phenyl]-1-cyclopropyl-2-(1,2,4-triazol-1-ypethanol (B.1.34), 2-[4-(4-chloro-phenoxy)-2-(trifluoromethyl)phenyl]-1-(1,2,4-triazol-1-yl)butan-2-ol (B.1.35), 2-[2-chloro-4-(4-chlorophenoxy)phenyl]-1-(1,2,4-triazol-1-yl)butan-2-ol (B.1.36), 2-[4-(4-chlorophenoxy)-2-(trifluoromethyl)phenyl]-3-methyl-1-(1,2,4-triazol-1-yl)butan-2-ol (B.1.37), 2-[4-(4-chlorophenoxy)-2-(trifluoromethyl)phenyl]-1-(1,2,4-triazol-1-yl)propan-2-ol (B.1.38), 2-[2-chloro-4-(4-chlorophenoxy)phenyl]-3-methyl-1-(1,2,4-triazol-1-yl)butan-2-ol (B.1.39), 2-[4-(4-chlorophenoxy)-2-(trifluoromethyl)phenyl]-1-(1,2,4-triazol-1-yl)pentan-2-ol (B.1.40), 2-[4-(4-fluorophenoxy)-2-(trifluoromethyl)phenyl]-1-(1,2,4-triazol-1-yl)propan-2-ol (B.1.41)), 2-[2-chloro-4-(4-chlorophenoxy)phenyl]-1-(1,2,4-triazol-1-yl)

pent-3-yn-2-ol (B.1.51); imidazoles: imazalil (B.1.42), pefurazoate (B.1.43), prochloraz (B.1.44), triflumizol (B.1.45); pyrimidines, pyridines and piperazines: fenarimol (B.1.46), nuarimol (B.1.47), pyrifenox (B.1.48), triforine (B.1.49), [3-(4-chloro-2-fluoro-phenyl)-5-(2, 4-difluorophenypisoxazol-4-yl]-(3-pyridyl)methanol (B.1.50);

Delta14-reductase inhibitors selected from: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitor of 3-keto reductase: fenhexamid (B.3.1);

C) Nucleic acid synthesis inhibitors phenylamides or acyl amino acid fungicides selected from: benalaxyl (C.1.1), benalaxyl-M (C.1.2), kiralaxyl (C.1.3), metalaxyl (C.1.4), metalaxyl-M (mefenoxam, C.1.5), ofurace (C.1.6), oxadixyl (C.1.7);

others selected from: hymexazole (C.2.1), octhilinone (C.2.2), oxolinic acid (C.2.3), bupirimate (C.2.4), 5-fluorocytosine (C.2.5), 5-fluoro-2-(p-tolylmethoxy) pyrimidin-4-amine (C.2.6), 5-fluoro-2-(4-fluorophenylmethoxy)pyrimidin-4-amine (C.2.7);

D) Inhibitors of cell division and cytoskeleton tubulin inhibitors selected from: benomyl (D1.1), carbendazim (D1.2), fuberidazole (D1.3), thiabendazole (D1.4), thiophanate-methyl (D1.5); triazolopyrimidines: 5-chloro-7-(4-methyl-piperidin-1-yl)-6-(2,4,6-trifluorophenyl)-[1,2,4]triazolo[1,5-a]pyrimidine (D1.6);

other cell division inhibitors selected from: diethofencarb (D2.1), ethaboxam (D2.2), pencycuron (D2.3), fluopicolide (D2.4), zoxamide (D2.5), metrafenone (D2.6), pyriofenone (D2.7);

E) Inhibitors of amino acid and protein synthesis methionine synthesis inhibitors (anilino-pyrimidines) selected from: cyprodinil (E.1.1), mepanipyrim (E.1.2), pyrimethanil (E.1.3);

protein synthesis inhibitors selected from: blasticidin-S (E.2.1), kasugamycin (E.2.2), kasugamycin hydrochloride-hydrate (E.2.3), mildiomycin (E.2.4), streptomycin (E.2.5), oxytetracyclin (E.2.6), polyoxine (E.2.7), validamycin A (E.2.8);

F) Signal transduction inhibitors

MAP/histidine kinase inhibitors selected from: fluoroimid (F.1.1), iprodione (F.1.2), procymidone (F.1.3), vinclozolin (F.1.4), fenpiclonil (F.1.5), fludioxonil (F.1.6);

G protein inhibitor: quinoxyfen (F.2.1);

G) Lipid and membrane synthesis inhibitors

Phospholipid biosynthesis inhibitors selected from: edifenphos (G.1.1), iprobenfos (G.1.2), pyrazophos (G.1.3), isoprothiolane (G.1.4);

lipid peroxidation compounds selected from: dicloran (G.2.1), quintozene (G.2.2), tecnazene (G.2.3), tolclofos-methyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7) and N-(1-(1-(4-cyano-phenyl)ethanesulfonyl)-but-2-yl)carbamic acid-(4-fluorophenyl) ester (G.3.8);

compound affecting cell membrane permeability and fatty acides: propamocarb (G.4.1);

fatty acid amide hydrolase inhibitors selected from: oxathiapiprolin (G.5.1), 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5-yl}-3-chlorophenyl methanesulfonate (G.5.3);

H) Inhibitors with multi site action inorganic active substances selected from: Bordeaux mixture (H.1.1), copper acetate (H.1.2), copper hydroxide (H.1.3), copper oxychloride (H.1.4), basic copper sulfate (H.1.5), sulfur (H.1.6);

thio- and dithiocarbamates selected from: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organochlorine compounds selected from: anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11), N-(4-chloro-2-nitro-phenyl)-N-ethyl-4-methyl-benzenesulfonamide (H.3.12);

guanidines and others selected from: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H-[1,4]dithiino[2,3-c:5,6-c']dipyrrole-1,3,5,7(2H,6H)-tetraone (H.4.10);

I) Cell wall synthesis inhibitors inhibitors of glucan synthesis selected from: validamycin (I.1.1), polyoxin B (I.1.2);

melanin synthesis inhibitors: pyroquilon (I.2.1), tricyclazole (I.2.2), carpropamid (I.2.3), dicyclomet (I.2.4), fenoxanil (I.2.5);

J) Plant defence inducers selected from: acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), potassium or sodium bicarbonate (J.1.9);

K) Unknown mode of action selected from: bronopol (K.1.1), chinomethionat (K.1.2), cyflufenamid (K.1.3), cymoxanil (K.1.4), dazomet (K.1.5), debacarb (K.1.6), diclomezine (K.1.7), difenzoquat (K.1.8), difenzoquat-methylsulfate (K.1.9), diphenylamin (K.1.10), fenpyrazamine (K.1.11), flumetover (K.1.12), flusulfamide (K.1.13), flutianil (K.1.14), methasulfocarb (K.1.15), nitrapyrin (K.1.16), nitrothal-isopropyl (K.1.18), oxathiapiprolin (K.1.19), tolprocarb (K.1.20), oxin-copper (K.1.21), proquinazid (K.1.22), tebufloquin (K.1.23), tecloftalam (K.1.24), triazoxide (K.1.25), 2-butoxy-6-iodo-3-propylchromen-4-one (K.1.26), 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone (K.1.27), 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone (K.1.28), 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone (K.1.29), N-(cyclopropylmethoxyimino-(6-difluoromethoxy-2,3-difluoro-phenyl)-methyl)-2-phenyl acetamide (K.1.30), N'-(4-(4-chloro-3-trifluoromethyl-phenoxy)-2,5-dimethyl-phenyl)-N-ethyl-N-methyl formamidine (K.1.31), N'-(4-(4-fluoro-3-trifluoromethyl-phenoxy)-2,5-dimethyl-phenyl)-N-ethyl-N-methyl formamidine (K.1.32), N'-(2-methyl-5-trifluoromethyl-4-(3-trimethylsilanyl-propoxy)-phenyl)-N-ethyl-N-methyl formamidine (K.1.33), N'-(5-difluoromethyl-2-methyl-4-(3-trimethylsilanyl-propoxy)-phenyl)-N-ethyl-N-methyl formamidine (K.1.34), methoxy-acetic acid 6-tert-butyl-8-fluoro-2,3-dimethyl-quinolin-4-yl ester (K.1.35), 3-[5-(4-methylphenyl)-2,3-dimethyl-isoxazolidin-3-yl]-pyridine (K.1.36), 3-[5-(4-chloro-phenyl)-2,3-dimethyl-isoxazolidin-3-yl]pyridine (pyrisoxazole) (K.1.37), N-(6-methoxy-pyridin-3-yl)cyclopropanecarboxylic acid amide (K.1.38), 5-chloro-1-(4,6-dimethoxy-pyrimidin-2-yl)-2-methyl-1H-benzoimidazole (K.1.39), 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate (K.1.40), picarbutrazox (K.1.41), pentyl N-[6-[[(Z)-[(1-methyltetrazol-5-yl)-phenyl-methylene]amino]oxymethyl]-2-pyridyl]carbamate (K.1.42), 2-[2-[(7,8-difluoro-2-methyl-3-quinolyl)oxy]-6-fluoro-phenyl]propan-2-ol (K.1.43), 2-[2-fluoro-6-[(8-fluoro-2-methyl-3-quinolyl)oxy]phen-yl]propan-2-ol (K.1.44), 3-(5-fluoro-3,3,4,4-tetramethyl-3,4-dihydroisoquinolin-1-yl)quinoline (K.1.45), 3-(4,4-difluoro-3,3-dimethyl-3,4-dihydroisoquinolin-1-yl)quinoline (K.1.46), 3-(4,4,5-trifluoro-3,3-dimethyl-3,4-dihydroisoquinolin-1-yl) quinoline (K.1.47), 9-fluoro-2,2-dimethyl-5-(3-quinolyl)-3H-1,4-benzoxazepine (K.1.48);

L) Biopesticides

L1) Microbial pesticides with fungicidal, bactericidal, viricidal and/or plant defense activator activity selected from: *Ampelomyces quisqualis, Aspergillus flavus, Aureobasidium pullulans, Bacillus altitudinis, B. amyloliquefaciens, B. megaterium, B. mojavensis, B. mycoides, B. pumilus, B. simplex, B. solisalsi; B. subtilis, B. subtilis* var. *amyloliquefaciens, Candida oleophlla, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea f. catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus alvei, Paenibacillus polymyxa, P. agglomerans, Pantoea vagans, Penicillium bilaiae, Phlebiopsis gigantea, Pseudomonas* sp., *Pseudomonas chloraphis, P. fluorescens, P. putida, Pseudozyma flucculosa, Pichia anomala, Pythium oligandrum, Sphaerodes mycoparasitica, Streptomyces griseoviridis, S. lydicus, S. violaceusniger, Talaromyces flavus, Typhula phacorrhiza, Ulocladium oudemansii, Verticillium dahlia,* zucchini yellow mosaic virus (avirulent strain);

L2) Biochemical pesticides with fungicidal, bactericidal, viricidal and/or plant defense activator activity selected from: chitosan (hydrolysate), harpin protein, laminarin, Menhaden fish oil, natamycin, Plum pox virus coat protein, potassium or sodium bicarbonate, *Reynoutria sachalinensis* extract, salicylic acid, tea tree oil;

L3) Microbial pesticides with insecticidal, acaricidal, molluscidal and/or nematicidal activity selected from: *Agrobacterium radiobacter, Bacillus cereus, B. firmus, B. thuringiensis, B. thuringiensis* ssp. *aizawai, B. t.* ssp. *israelensis, B. t.* ssp. *galleriae, B. t.* ssp. *kurstaki, B. t.* ssp. *tenebrionis, Beauveria bassiana, B. brongniartii, Burkholderia* spp., *Chromobacterium subtsugae, Cydia pomonella* granulovirus (CpGV), *Cryptophlebia leucotreta* granulovirus (CrleGV), *Flavobacterium* spp., *Helicoverpa armigera* nucleopolyhedrovirus (HearNPV), *Heterorhabditis bacteriophora, Isaria fumosorosea, Lecanicillium longisporum, L. muscarium, Metarhizium anisopliaze, Metarhizium anisopliae* var. *anisopliae, M. anisopliae* var. *acridum, Nomuraea rileyi; Paecilomyces lilacinus, Paenibacillus popilliae, Pasteuria* spp., *P. nishizawae, P. penetrans, P. ramosa, P. thornea, P. usgae, Pseudomonas fluorescens, Spodoptera littoralis* nucleopolyhedrovirus (SpliNPV), *Steinernema carpocapsae, S. feltiae, S. kraussei, Streptomyces galbus, S. microflavus;*

L4) Biochemical pesticides with insecticidal, acaricidal, molluscidal, pheromone and/or nematicidal activity selected from: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulylsenecioate, cis-jasmone, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-ylacetate, Z-7-tetradecen-2-one, Z-9-tetradecen-1-ylacetate, Z-11-tetradecenal, Z-11-tetradecen-1-ol, *Acacia negra* extract, extract of grapefruit seeds and pulp, extract of *Chenopodium ambrosiodes,* Catnip oil, Neem oil, Quillay extract, Tagetes oil;

L5) Microbial pesticides with plant stress reducing, plant growth regulator, plant growth promoting and/or yield enhancing activity selected from: *Azospirillum amazonense, A. brasilense, A. lipoferum, A. irakense, A. halopraeferens, Bradyrhizobium* spp., *B. elkanii, B. japonicum, B. liaoningense, B. lupini, Delftia acidovorans, Glomus intraradices, Mesorhizobium* spp., *Rhizobium leguminosarum* bv. *phaseoli, R. I.* bv. *trifolii, R. I.* bv. *viciae, R. tropici, Sinorhizobium meliloti,*

L6) Biochemical pesticides with plant stress reducing, plant growth regulator and/or plant yield enhancing activity selected from: abscisic acid, aluminium silicate (kaolin), 3-decen-2-one, formononetin, genistein, hesperetin, homobrassinolide, humates, jasmonic acid and its salts or derivatives thereof, lysophosphatidyl ethanolamine, naringenin, polymeric polyhydroxy acid, *Ascophyllum nodosum* (Norwegian kelp, Brown kelp) extract and *Ecklonia maxima* (kelp) extract;

M) Growth regulators selected from: abscisic acid (M.1.1), amidochlor, ancymidol, 6-benzyl-aminopurine, brassinolide, butralin, chlormequat, chlormequat chloride, choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat, mepiquat chloride, naphthaleneacetic acid, N-6-benzyladenine, paclobutrazol, prohexadione, prohexadione-calcium, prohydrojasmon, thidiazuron, triapenthenol, tributyl phosphorotrithioate, 2,3,5-tri-iodobenzoic acid, trinexapac-ethyl and uniconazole;

N) Herbicides
acetamides selected from: acetochlor (N.1.1), alachlor, butachlor, dimethachlor, dimethenamid (N.1.2), flufenacet (N.1.3), mefenacet (N.1.4), metolachlor (N.1.5), metazachlor (N.1.6), napropamide, naproanilide, pethoxamid, pretilachlor, propachlor, thenylchlor;
amino acid derivatives selected from: bilanafos, glyphosate (N.2.1), glufosinate (N.2.2), sulfosate (N.2.3);

aryloxyphenoxypropionates: clodinafop (N.3.1), cyhalofop-butyl, fenoxaprop (N.3.2), fluazifop (N.3.3), haloxyfop (N.3.4), metamifop, propaquizafop, quizalofop, quizalofop-P-tefuryl;

Bipyridyls: diquat, paraquat (N.4.1);

(thio)carbamates selected from: asulam, butylate, carbetamide, desmedipham, dimepiperate, eptam (EPTC), esprocarb, molinate, orbencarb, phenmedipham (N.5.1), prosulfocarb, pyributicarb, thiobencarb, triallate;

cyclohexanediones selected from: butroxydim, clethodim (N.6.1), cycloxydim (N.6.2), profoxydim (N.6.3), sethoxydim (N.6.4), tepraloxydim (N.6.5), tralkoxydim;

dinitroanilines selected from: benfluralin, ethalfluralin, oryzalin, pendimethalin (N.7.1), prodiamine (N.7.2), trifluralin (N.7.3);

diphenyl ethers selected from: acifluorfen (N.8.1), aclonifen, bifenox, diclofop, ethoxyfen, fomesafen, lactofen, oxyfluorfen;

hydroxybenzonitriles selected from: bomoxynil (N.9.1), dichlobenil, ioxynil;

imidazolinones selected from: imazamethabenz, imazamox (N.10.1), imazapic (N.10.2), imazapyr (N.10.3), imazaquin (N.10.4), imazethapyr (N.10.5);

phenoxy acetic acids selected from: clomeprop, 2,4-dichlorophenoxyacetic acid (2,4-D) (N.11.1), 2,4-DB, dichlorprop, MCPA, MCPA-thioethyl, MCPB, Mecoprop;

pyrazines selected from: chloridazon (N.11.1), flufenpyrethyl, fluthiacet, norflurazon, pyridate;

pyridines selected from: aminopyralid, clopyralid (N.12.1), diflufenican, dithiopyr, fluridone, fluroxypyr (N.12.2), picloram (N.12.3), picolinafen (N.12.4), thiazopyr;

sulfonyl ureas selected from: amidosulfuron, azimsulfuron, bensulfuron (N.13.1), chlorimuron-ethyl (N.13.2), chlorsulfuron, cinosulfuron, cyclosulfamuron (N.13.3), ethoxysulfuron, flazasulfuron, flucetosulfuron, flupyrsulfuron, foramsulfuron, halosulfuron, imazosulfuron, iodosulfuron (N.13.4), mesosulfuron (N.13.5), metazosulfuron, metsulfuron-methyl (N.13.6), nicosulfuron (N.13.7), oxasulfuron, primisulfuron, prosulfuron, pyrazosulfuron, rimsulfuron (N.13.8), sulfometuron, sulfosulfuron, thifensulfuron, triasulfuron, tribenuron, trifloxysulfuron, triflusulfuron (N.13.9), tritosulfuron, 1-((2-chloro-6-propyl-imidazo[1,2-b]pyridazin-3-yl)sulfonyl)-3-(4,6-dimethoxy-pyrimidin-2-yl)urea;

triazines: ametryn, atrazine (N.14.1), cyanazine, dimethametryn, ethiozin, hexazinone (N.14.2), metamitron, metribuzin, prometryn, simazine, terbuthylazine, terbutryn, triaziflam;

ureas selected from: chlorotoluron, daimuron, diuron (N.15.1), fluometuron, isoproturon, linuron, methabenzthiazuron, tebuthiuron;

other acetolactate synthase inhibitors selected from: bispyribac-sodium, cloransulam-methyl, diclosulam, florasulam (N.16.1), flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone (N.16.2), pyroxsulam;

others selected from: amicarbazone, aminotriazole, anilofos, beflubutamid, benazolin, bencarbazone, benfluresate, benzofenap, bentazone (N.17.1), benzobicyclon, bicyclopyrone, bromacil, bromobutide, butafenacil, butamifos, cafenstrole, carfentrazone, cinidon-ethyl (N.17.2), chlorthal, cinmethylin (N.17.3), clomazone (N.17.4), cumyluron, cyprosulfamide, dicamba (N.17.5), difenzoquat, diflufenzopyr (N.17.6), *Drechslera monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac (N.17.7), quinmerac (N.17.8), mesotrione (N.17.9), methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil (N.17.10), sulcotrione (N.17.11), sulfentrazone, terbacil, tefuryltrione, tembotrione, thiencarbazone, topramezone (N.17.12), (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester;

O) Insecticides organo(thio)phosphates selected from: acephate (O.1.1), azamethiphos (O.1.2), azinphos-methyl (O.1.3), chlorpyrifos (O.1.4), chlorpyrifos-methyl (O.1.5), chlorfenvinphos (O.1.6), diazinon (O.1.7), dichlorvos (O.1.8), dicrotophos (O.1.9), dimethoate (O.1.10), disulfoton (O.1.11), ethion (O.1.12), fenitrothion (O.1.13), fenthion (O.1.14), isoxathion (O.1.15), malathion (O.1.16), methamidophos (O.1.17), methidathion (O.1.18), methyl-parathion (O.1.19), mevinphos (O.1.20), monocrotophos (O.1.21), oxydemetonmethyl (O.1.22), paraoxon (O.1.23), parathion (O.1.24), phenthoate (O.1.25), phosalone (O.1.26), phosmet (O.1.27), phosphamidon (O.1.28), phorate (O.1.29), phoxim (O.1.30), pirimiphos-methyl (O.1.31), profenofos (O.1.32), prothiofos (O.1.33), sulprophos (O.1.34), tetrachlorvinphos (O.1.35), terbufos (O.1.36), triazophos (O.1.37), trichlorfon (O.1.38);

carbamates selected from: alanycarb (O.2.1), aldicarb (O.2.2), bendiocarb (O.2.3), benfuracarb (O.2.4), carbaryl (O.2.5), carbofuran (O.2.6), carbosulfan (O.2.7), fenoxycarb (O.2.8), furathiocarb (O.2.9), methiocarb (O.2.10), methomyl (O.2.11), oxamyl (O.2.12), pirimicarb (O.2.13), propoxur (O.2.14), thiodicarb (O.2.15), triazamate (O.2.16);

pyrethroids selected from: allethrin (O.3.1), bifenthrin (0.3.2), cyfluthrin (O.3.3), cyhalothrin (O.3.4), cyphenothrin (O.3.5), cypermethrin (O.3.6), alpha-cypermethrin (O.3.7), beta-cypermethrin (O.3.8), zeta-cypermethrin (O.3.9), deltamethrin (O.3.10), esfenvalerate (O.3.11), etofenprox (O.3.11), fenpropathrin (O.3.12), fenvalerate (O.3.13), imiprothrin (O.3.14), lambda-cyhalothrin (O.3.15), permethrin (O.3.16), prallethrin (O.3.17), pyrethrin I and II (O.3.18), resmethrin (O.3.19), silafluofen (O.3.20), tau-fluvalinate (O.3.21), tefluthrin (O.3.22), tetramethrin (O.3.23), tralomethrin (O.3.24), transfluthrin (O.3.25), profluthrin (O.3.26), dimefluthrin (O.3.27);

insect growth regulators selected from: a) chitin synthesis inhibitors: benzoylureas: chlorfluazuron (O.4.1), cyramazin (O.4.2), diflubenzuron (O.4.3), flucycloxuron (O.4.4), flufenoxuron (O.4.5), hexaflumuron (O.4.6), lufenuron (O.4.7), novaluron (O.4.8), teflubenzuron (O.4.9), triflumuron (O.4.10); buprofezin (O.4.11), diofenolan (O.4.12), hexythiazox (O.4.13), etoxazole (O.4.14), clofentazine (O.4.15); b) ecdysone antagonists: halofenozide (O.4.16), methoxyfenozide (O.4.17), tebufenozide (O.4.18), azadirachtin (O.4.19); c) juvenoids: pyriproxyfen (O.4.20), methoprene (O.4.21), fenoxycarb (O.4.22); d) lipid biosynthesis inhibitors: spirodiclofen (O.4.23), spiromesifen (O.4.24), spirotetramat (O.4.24);

nicotinic receptor agonists/antagonists compounds selected from: clothianidin (O.5.1), dinotefuran (O.5.2), flupyradifurone (O.5.3), imidacloprid (O.5.4), thiamethoxam (O.5.5), nitenpyram (O.5.6), acetamiprid (O.5.7), thiacloprid (O.5.8), 1-2-chloro-thiazol-5-ylmethyl)-2-nitrimino-3,5-dimethyl-[1,3,5]triazinane (O.5.9);

GABA antagonist compounds selected from: endosulfan (O.6.19, ethiprole (O.6.2), fipronil (O.6.3), vaniliprole (O.6.4), pyrafluprole (O.6.5), pyriprole (O.6.6), 5-amino-1-(2,6-dichloro-4-methyl-phenyl)-4-sulfinamoyl-1H-pyrazole-3-carbothioic acid amide (O.6.7);

macrocyclic lactone insecticides selected from: abamectin (O.7.1), emamectin (O.7.2), milbemectin (O.7.3), lepimectin (O.7.4), spinosad (O.7.5), spinetoram (O.7.6);

mitochondrial electron transport inhibitor (METI) I acaricides selected from: fenazaquin (O.8.1), pyridaben (O.8.2), tebufenpyrad (O.8.3), tolfenpyrad (O.8.4), flufenerim (O.8.5);

METI II and III compounds: acequinocyl (O.9.1), fluacyprim (O.9.2), hydramethylnon (O.9.3);

Uncoupler: chlorfenapyr (O.10.1);

oxidative phosphorylation inhibitors selected from: cyhexatin (O.11.1), diafenthiuron (O.11.2), fenbutatin oxide (O.11.3), propargite (O.11.4);

moulting disruptor compound: cryomazine (O.12.1);

mixed function oxidase inhibitor: piperonyl butoxide (O.13.1);

sodium channel blockers selected from: indoxacarb (O.14.1), metaflumizone (O.14.2);

ryanodine receptor inhibitors selected from: chlorantraniliprole (O.15.1), cyantraniliprole (O.15.2), flubendiamide (O.15.3), N-[4,6-dichloro-2-[(diethyl-lambda-4-sulfanylidene)carba-moyl]-phenyl]-2-(3-chloro-2-pyridyl)-5-(trifluoromethyl)pyrazole-3-carboxamide (O.15.4); N-[4-chloro-2-[(diethyl-lambda-4-sulfanylidene)carbamoyl]-6-Methyl-phenyl]-2-(3-chloro-2-pyridyl)-5-(trifluoromethyppyrazole-3-carboxamide (O.15.5); N-[4-chloro-2-[(di-2-propyl-lambda-4-sulfanylidene)carbamoyl]-6-methyl-phenyl]-2-(3-chloro-2-pyridyl)-5-(trifluoro-methyl)pyrazole-3-carboxamide (O.15.6); N-[4,6-dichloro-2-[(di-2-propyl-lambda-4-sulfanylidene)carbamoyl]-phenyl]-2-(3-chloro-2-pyridyl)-5-(trifluoromethyppyrazole-3-carboxamide (O.15.7); N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide (O.15.8); N-[4,6-dibromo-2-[(di-2-propyl-lambda-4-sulfanylidene)carbamoyl]-phenyl]-2-(3-chloro-2-pyridyl)-5-(trifluoromethyppyrazole-3-carboxamide (O.15.9); N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide (O.15.10); N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide (O.15.11);

others selected from: benclothiaz (O.16.1), bifenazate (O.16.2), artap (O.16.3), flonicamid (O.16.4), pyridalyl (O.16.5), pymetrozine (O.16.6), sulfur (O.16.7), thiocyclam (O.16.8), cyenopyrafen (O.16.9), flupyrazofos (O.16.10), cyflumetofen (O.16.11), amidoflumet (O.16.12), imicyafos (O.16.13), bistrifluron (O.16.14), pyrifluquinazon (O.16.15) and 1,1'-[(3S,4R,4aR,6S,6aS,12R,12aS,12bS)-4-[[(2-cyclopropylacetypoxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl] cyclopropaneacetic acid ester (O.16.16).

According to one embodiment, the mixtures comprise at least one microorganism of the genus *Bacillus* seleted from *B. amyloliquefaciens* AP-136 (NRRL B-50330; NRRL B-50614), *B. amyloliquefaciens* AP-188 (NRRL B-50331; NRRL B-50615), *B. amyloliquefaciens* AP-218 (NRRL B-50618), *B. amyloliquefaciens* AP-219 (NRRL B-50332, NRRL B-50619), *B. amyloliquefaciens* AP-295 (NRRL B-50333, NRRL B-50620) *B. mojavensis* AP-209 (NRRL B-50616), and *B. solisalsi* AP-217 (NRRL B-50617) (which are herein also referred to as AP-136, AP-188, AP-218, AP-219, AP-295, AP-209 and AP-217, respectively); and at least one pesticide II in a synergistically effective amount.

The invention also relates to a method for controlling phytopathogenic harmful fungi using mixtures of at least one microorganism selected from AP-136, AP-188, AP-218, AP-219, AP-295, AP-209 and AP-217 and and at least one pesticide II and to the use of microorganisms I and pesticides II for preparing such mixtures, and to compositions comprising these mixtures and seed comprising these mixtures or coated with this this mixture.

Moreover, we have found that simultaneous, that is joint or separate, application of at least one microorganism I and a pesticide II or successive application of at least one microorganism I and of a pesticide II allows better control of harmful fungi than is possible with the individual components alone (synergistic mixtures).

When applying the at least one microorganism I and a pesticide II sequentially the time between both applications may vary e.g. between 2 hours and 7 days. Also a broader range is possible ranging from 0.25 hour to 30 days, preferably from 0.5 hour to 14 days, particularly from 1 hour to 7 days or from 1.5 hours to 5 days, even more preferred from 2 hours to 1 day. Preferably, the at least one microorganism I is applied as last treatment.

Component 1) in the mixtures embraces not only the isolated, pure cultures of at least one microorganism I as defined herein, but also a its cell-free extract having pesticidal activity, preferably a ketone-based extract, its suspensions in a whole broth culture or as a metabolite-containing supernatant or a purified metabolite obtained from a whole broth culture of the microorganism or microorganism strain.

As used herein, "whole culture broth" refers to a liquid culture of a microorganism containing vegetative cells and/or spores suspended in the culture medium and optionally metabolites produced by the respective microorganism.

As used herein, "strain" refers to isolate or a group of isolates exhibiting phenotypic and/or genotypic traits belonging to the same lineage, distinct from those of other isolates or strains of the same species.

According to a further embodiment, component 1) is at least one microorganism selected from AP-136, AP-188, AP-218, AP-219, AP-295, AP-209 and AP-217, and a cell-free extract of the aforementioned strains. According to a further embodiment, component 1) is at least one microorganism selected from AP-136, AP-188, AP-218, AP-219, AP-295, AP-209 and AP-217. According to a further embodiment, component 1) is at least one microorganism selected from AP-136, AP-188, AP-218, AP-219, AP-295, AP-209 and AP-217 in a whole browth. According to a further embodiment, component 1) is at least one microorganism selected from AP-136, AP-188, AP-218, AP-219, AP-295, AP-209 and AP-217 in a dormant form. According to a further embodiment, component 1) is at least one microorganism selected from AP-136, AP-188, AP-218, AP-219, AP-295, AP-209 and AP-217 in the form of spores.

The microorganisms AP-136, AP-188, AP-218, AP-219, AP-295, AP-209 and AP-217 can be cultivated e.g. using Potato dextrose agar (PDA) under aerobvic growth conditions at about 28° C. In large liquid cultures, aeriation may be necessary. The bacterial cells (vegatitive cells and spores) can be washed and concentrated (e.g. by centrifugation at room temperature for about 15 min at 7000×g). To produce a dry formulation, bacterial cells, preferably spores were suspended in a suitable dry carrier (e.g. clay). To produce a liquid formulation, cells, preferably spores, can be re-suspended in a suitable liquid carrier (e.g. water-based) to the desired spore density. The spore density number of spores per mL can be determined by identifying the number of colony-forming units (CFU) on agar medium e.g. potato dextrose agar after incubation for several days at 28° C. The microorganism I are generally active in temperatures between 5° C. and 50° C., preferably between 15° C. and 35° C.

According to a further embodiment, component 1) is at least one microorganism I selected from *Bacillus amyloliquefaciens* AP-136 (NRRL B-50330; NRRL B-50614), *B. amyloliquefaciens* AP-188 (NRRL B-50331; NRRL B-50615), *B. amyloliquefaciens* AP-218 (NRRL B-50618), *B. amyloliquefaciens* AP-219 (NRRL B-50332, NRRL B-50619), and *B. amyloliquefaciens* AP-295 (NRRL B-50333, NRRL B-50620); in particular *B. amyloliquefaciens* AP-188.

According to a further embodiment, component 1) is at least one microorganism I selected from *B. mojavensis* AP-209 (NRRL B-50616) and *B. solisalsi* AP-217 (NRRL B-50617).

According to a further embodiment, component 2) is selected from *Bradyrhizobium japonicum*, *B. elkanii*, *Bradyrhizobium* spp., *Bradyrhizobium* sp. (*Arachis*), *Bradyrhizobium* sp. (*Vigna*), *B. liaoningense*, *B. lupine*; *Azospirillum brasilense*, *A. amazonense*, *A. lipoferum*, *A. irakense*, *A. halopraeferens*; *Delftia acidovorans*, *Glomus intraradices*; *Mesorhizobium* spp., *Mesorhizobium ciceri*, *M. huakii*, *M. loti*; *Rhizobium leguminosarum* bv. *phaseoli*, *R. leguminosarum* bv. *trifolii*, *R. leguminosarum* bv. *viciae*, *R. tropici*, *Sinorhizobium mellloti*; *Bacillus amyloliquefaciens*, *B. amyloliquefaciens* ssp. *plantarum*, *B. firmus*, *B. pumilus*, *B. subtilis*, *B. simplex*, *B. megaterium*, *B. altitudinis*, *B. mojavensis*, *B. mycoides*, *B. solisalsi*, *Burkholderia* spp., *Coniothyrium minitans*, *Muscodor albus*, *Paecilomyces lilacinus*, *Paenibacillus alvei*, *Pasteuria nishizawa*, *Pasteuria usgae*, *Penicillium bilaiae*, *Pseudomonas fluorescens*, *Pseudomonas putida*; abscisic acid, jasmonic acid, its salts and derivatives thereof, cis-jasmone, methyl jasmonate; harpin protein.

According to a further embodiment, component 2) is selected from *Bradyrhizobium japonicum*, *B. elkanii*, *Azospinflum brasilense*; *Bacillus amyloliquefaciens*, *B. amyloliquefaciens* ssp. *plantarum*, *B. firmus*, *B. pumilus*, *B. subtilis*, *B. simplex*, *B. megaterium*; *Burkholderia* spp., *Coniothyrium minitans*, *Muscodor albus*, *Paecilomyces lilacinus*, *Paenibacillus alvei*, *Penicillium bilaiae*, *Pasteuria nishizawa*; cis-jasmone, methyl jasmonate and harpin protein.

According to a further embodiment, the mixtures comprise as component 2) at least one pesticide II selected from *Bradyrhizobium japonicum*, *B. elkanii*, *Azospirillum brasilense*; cis-jasmone, methyl jasmonate and harpin protein.

According to a further embodiment, component 2) is selected from *Bacillus firmus*, *B. pumilus*, *Burkholderia* spp., *Muscodor albus* and *Paecilomyces lilacinus*. These mixture are especially effective for control of nematodes.

According to a further embodiment, the mixture comprise in addition to component 1) and component 2) a further active component 3) which is selected from methyl jasmonate, cis-jasmone and harpin, provided that component 2) is different from component 3).

The biopesticides from group L) of pesticides II, their preparation and their pesticidal activity e. g. against harmful fungi or insects are known (e-Pesticide Manual V 5.2 (ISBN 978 1 901396 85 0) (2008-2011); http://www.epa.gov/opp00001/biopesticides/, see product lists therein; http://www.omri.org/omri-lists, see lists therein; Bio-Pesticides Database BPDB http://sitem.herts.ac.uk/aeru/bpdb/, see A to Z link therein).

The biopesticides from group L1) and/or L2) may also have insecticidal, acaricidal, molluscidal, pheromone, nematicidal, plant stress reducing, plant growth regulator, plant growth promoting and/or yield enhancing activity. The biopesticides from group L3) and/or L4) may also have fungicidal, bactericidal, viricidal, plant defense activator, plant stress reducing, plant growth regulator, plant growth promoting and/or yield enhancing activity. The biopesticides from group L5) and/or L6) may also have fungicidal, bactericidal, viricidal, plant defense activator, insecticidal, acaricidal, molluscidal, pheromone and/or nematicidal activity.

Many of these biopesticides have been deposited under deposition numbers mentioned herein (the prefices refer to the acronym of the respective culture collection), are referred to in literature, registered and/or are commercially available: aluminium silicate (Screen™ Duo from Certis LLC, USA), *Agrobacterium radiobacter* K1026 (e. g. NoGall® from BASF Agricultural Specialties Pty Ltd, Australia), *A. radiobacter* K84 (Nature 280, 697-699, 1979; e. g. GallTroll® from AG Biochem, Inc., C, USA), *Ampelomyces quisqualis* M-10 (e. g. AQ 10® from Intrachem Bio GmbH & Co. KG, Germany), *Ascophyllum nodosum* (Norwegian kelp, Brown kelp) extract or filtrate (e. g. ORKA GOLD from BASF Agricultural Specialities (Pty) Ltd., South Africa; or Goemar® from Laboratoires Goemar, France), *Aspergillus flavus* NRRL 21882 isolated from a peanut in Georgia in 1991 by USDA, National Peanut Research Laboratory (e. g. in Afla-Guard® from Syngenta, CH), mixtures of *Aureobasidium pullulans* DSM 14940 and DSM 14941 (e. g. blastospores in Blossom Protect® from bio-ferm GmbH, Germany), *Azospirillum amazonense* SpY2 (DN: BR 11140; Proc. 9$^{th}$ Int. and 1$^{st}$ Latin American PGPR meeting, Quimara, Medellín, Colombia 2012, p. 60, ISBN 978-958-46-0908-3), *A. brasllense* AZ39 (also called Az 39; INTA Az-39; Eur. J. Soil Biol 45(1), 28-35, 2009), *A. brasilense* XOH (e. g. AZOS from Xtreme Gardening, USA or RTI Reforestation Technologies International; USA), *A. brasilense* BR 11002 (Proc. 9$^{th}$ Int. and 1$^{st}$ Latin American PGPR meeting, Quimara, Medellín, Colombia 2012, p. 60, ISBN 978-958-46-0908-3), *A. brasilense* Sp245 (BR 11005; e. g. in GELFIX Gramíneas from BASF Agricultural Specialties Ltd., Brazil), *A. brasilense* strains Ab-V5 and Ab-V6

(e. g. in AzoMax from Novozymes BioAg Produtos papra Agricultura Ltda., Quattro Barras, Brazil or SimbioseMaíz® from Simbiose-Agro, Cruz Alta, RS, Brazil; Plant Soil 331, 413-425, 2010), *A. lipoferum* BR 11646 (Sp31) (Proc. 9$^{th}$ Int. and 1$^{st}$ Latin American PGPR meeting, Quimara, Medellín, Colombia 2012, p. 60), *Bacillus altitudinis* 41KF2b (DSM 21631; Int. J. Syst. Evol. Microbiol. 56(7), 1465-1473, 2006), *Bacillus amyloliquefaciens* strains AP-136 (NRRL B-50614 and B-50330), AP-188 (NRRL B-50615 and B-50331), AP-218 (NRRL B-50618), AP-219 (NRRL B-50619 and B-50332), and AP-295 (NRRL B-50620 and B-50333) all known from U.S. Pat. No. 8,445,255; *B. amyloliquefaciens* IT-45 (CNCM I-3800) (e. g. Rhizocell C from ITHEC, France), *B. amyloliquefaciens* IN937a (J. Microbiol. Biotechnol. 17(2), 280-286, 2007; e. g. BioYield® from Gustafson LLC, TX, USA), *B. amyloliquefaciens* spp. *plantarum* D747 (US 20130236522 A1; FERM BP-8234; e. g. Double Nickel™ 55 WDG or Double Nickel™ LC from Certis LLC, USA), *B. amyloliquefaciens* spp. *plantarum* FZB24 isolated from plant pathogen-infested soil of a sugar beet field in Brandenburg, Germany (also called SB3615; DSM ID 96-2; J. Plant Dis. Prot. 105, 181-197, 1998; e. g. Taegro® from Novozyme Biologicals, Inc., USA), *B. amyloliquefaciens* spp. *plantarum* SB3615vPPI being a phage-resistant variant of FZB24 (MRRL B-50349; US 2011/023045 A1; from Novozyme Biologicals, Inc., USA), *B. amyloliquefaciens* ssp. *plantarum* FZB42 isolated from plant pathogen-infested soil of a sugar beet field in Brandenburg, Germany (J. Plant Dis. Prot. 105, 181-197, 1998; DSM 23117; e. g. RhizoVital® 42 from AbiTEP GmbH, Berlin, Germany), *B. amyloliquefaciens* ssp. *plantarum* GB03 (also called GBO3; ATCC SD-1397; Phytopathol. 86(11), S36, 1996; e. g. Kodiak® or BioYield® from Gustafson, Inc., USA; or Companion® from Growth Products, Ltd., White Plains, N.Y. 10603, USA), *B. amyloliquefaciens* ssp. *plantarum* MB1600 also referred to as 1430 (NRRL B-50595; Int. J. Microbiol. Res. 3(2) (2011), 120-130; US 2012/0149571 A1; e. g. Integral®, Subtilex® NG from BASF Corp., USA), *B. amyloliquefaciens* spp. *plantarum* TJ1000 (also called 1BE; CA 2471555 A1; ATCC BAA-390; e. g. QuickRoots™ from TJ Technologies, Watertown, S. Dak., USA), *B. cereus* CNCM I-1562 (U.S. Pat. No. 6,406,690), *B. chitinosporus* AQ746 isolated from roots in Saskatchewan, Canada (NRRL B-21618; U.S. Pat. No. 5,733,544; AgraQuest now Bayer CropScience LP, USA), *B. firmus* CNCM I-1582 (WO 2009/126473, WO 2009/124707, U.S. Pat. No. 6,406,690; e. g. Votivo® from Bayer CropScience LP, USA), *B. megaterium* strains H491 (NRRL B-50769), M018 (NRRL B-50770) and J142 (NRRL B-50771) all known from US 2014/0051571 A1 from Marrone BioInnovations, Inc., USA; *B. mojavensis* AP-209 (NRRL B-50616; U.S. Pat. No. 8,445,255), *B. mycoides* AQ726 (NRRL B-21664; U.S. Pat. No. 5,906,818; from Bayer Crop Science, Germany), *B. mycoides* strain J (e.g. BmJ WG from Certis, USA against potato virus Y), *B. pumilus* GB34 (ATCC 700814; e. g. YieldShield® from Gustafson LLC, TX, USA), *B. pumilus* GHA 180 isolated from apple tree rhizosphere in Mexico (IDAC 260707-01; e. g. in PRO-MIX® BX from Premier Horticulture, 1, avenue Premier, Rivie're-du-Loup, Quebec, Canada G5R6C1), *B. pumilus* KFP9F (NRRL B-50754; WO 2014/029697; e. g. BAC-UP or FUSION-P from BASF Agricultural Specialities (Pty) Ltd., South Africa), *B. pumilus* INR-7 otherwise referred to as BU-F22 and BU-F33 (NRRL B-50185, NRRL B-50153; U.S. Pat. No. 8,445,255), *B. pumilus* QST 2808 (NRRL B-30087; e. g. Sonata® or Ballad® Plus from AgraQuest Inc., USA), *B. solisalsi* AP-217 (NRRL B-50617; U.S. Pat. No. 8,445,255), *B. subtilis* CX-9060 (Federal Register 77(7), 1633-1637; by Certis U.S.A., L.L.C.), *B. subtilis* FB17 also called UD 1022 or UD10-22 isolated from red beet roots in North America (ATCC PTA-11857; System. Appl. Microbiol. 27, 372-379, 2004; US 2010/0260735; WO 2011/109395); *B. subtilis* GB07 (Phytopathol. 86(11), S36, 1996; Epic® from Gustafson, Inc., USA), *B. subtilis* QST-713 isolated from a California peach orchard in 1995 (NRRL B-21661; e. g. Rhapsody®, Serenade® MAX or Serenade® ASO from AgraQuest Inc., USA), *B. thuringiensis* ssp. *aizawai* ABTS-1857 (also called ABG-6346; ATCC SD-1372; e. g. XenTari® from BioFa AG, Munsingen, Germany), *B. t.* ssp. *aizawai* SAN 401 I, ABG-6305 (WO 2013/087709); *Bacillus t.* ssp. *israelensis* AM65-52 of Serotype H-14 (ATCC SD-1276; e. g. Vecto-Bac® from Valent BioSciences, IL, USA), *Bacillus thuringiensis* ssp. *kurstaki* SB4 (NRRL B-50753; e. g. Beta Pro® from BASF Agricultural Specialities (Pty) Ltd., South Africa), *B. t.* ssp. *kurstaki* ABTS-351 identical to HD-1 (ATCC SD-1275; e. g. Dipel® DF from Valent BioSciences, IL, USA), *B. t.* ssp. *kurstaki* EG 2348 (NRRL B-18208; e. g. Lepinox® or Rapax® from CBC (Europe) S.r.l., Italy), *B. t.* ssp. *tenebrionis* DSM 2803 of Serotype H 8a, 8b (identical to NRRL B-15939; EP 0 585 215 B1; Mycogen Corp.), *B. t.* ssp. *tenebrionis* NB-125 (also referred to as SAN 418 I or ABG-6479; EP 0 585 215 B1; DSM 5526; former production strain of Novo-Nordisk), *B. t.* ssp. *tenebrionis* NB-176 (or NB-176-1; a gamma-irradiated, induced high-yielding mutant of strain NB-125; EP 585 215 B1; DSM 5480; e. g. Novodor® from Valent BioSciences, Switzerland), *Beauveria bassiana* JW-1 (ATCC 74040; e. g. Naturalis® from CBC (Europe) S.r.l., Italy), *B. bassiana* DSM 12256 (US 200020031495; e. g. BioExpert® SC from Live Sytems Technology S.A., Colombia), *B. bassiana* GHA (ATCC 74250; e. g. BotaniGard® 22WGP from Laverlam Int. Corp., USA), *B. bassiana* PPRI 5339 (ARSEF 5339; NRRL 50757; e. g. BroadBand® from BASF Agricultural Specialities (Pty) Ltd., South Africa), *B. brongniartii* for control of cockchafer (J. Appl. Microbiol. 100(5),1063-72, 2006; e. g. Melocont® from Agrifutur, Agrianello, Italy), *Bradyrhizobium* sp. (e. g. Vault® from BASF Corp., USA), *B.* sp. (*Arachis*) CB1015 presumably originally collected in India (IITA 1006, USDA 3446; from Australian Inoculants Research Group; http://www.qaseeds.com.au/inoculant_applic.php). *B.* sp. (*Arachis*) strains deposited at SEMIA and known from FEMS Microbiol. Letters 303(2), 123-131, 2010; Revista Brasileira de Ciencia do Solo 35(3), 739-742, 2011, ISSN 0100-0683: SEMIA 6144, SEMIA 6462 (BR 3267) and SEMIA 6464 (BR 3262); *B.* sp. (*Vigna*) PNLO1 (Bisson and Mason, Apr. 29, 2010, Project report, Worcester Polytechnic Institute, Worcester, Mass., USA: http://www-.wpi.edu/Pubs/E-project/Available/E-project-042810-163614/; e. g. Vault® Peanut Liquid from BASF Corp., USA), *B. elkanii* SEMIA 587 (Appl. Environ. Microbiol. 73(8), 2635, 2007; e. g. GELFIX 5 from BASF Agricultural Specialties Ltd., Brazil), *B. elkanii* SEMIA 5019 (=29W; Appl. Environ. Microbiol. 73(8), 2635, 2007; e. g. GELFIX 5 from BASF Agricultural Specialties Ltd., Brazil), *B. elkanii* USDA 76, *B. elkanii* USDA 94*B. elkanii* USDA 3254, *B. elkanii* U-1301 and U-1302 (e. g. Nitragin® Optimize from Novozymes Bio As S.A., Brazil, or Nlitrasec for soybean from LAGE y Cia, Brazil), *B. japonicum* (e. g. VAULT® from BASF Corp., USA), *B. japonicum* 532c isolated from Wisconsin field (Nitragin 61A152; Can. J. Plant. Sci. 70, 661-666, 1990; e. g. in Rhizoflo®, Histick®, Hicoat® Super from BASF Agricultural Specialties Ltd., Canada), *B. japonicum* E-109 variant of strain USDA 138

(INTA E109, SEMIA 5085; Eur. J. Soil Biol. 45, 28-35, 2009; Biol. Fertil. Soils 47, 81-89, 2011), *B. japonicum* G49 (MSDJ G49; C. R. Acad. Agric. Fr. 73, 163-171, 1987); *B. japonicum* strains deposited at SEMIA known from Appl. Environ. Microbiol. 73(8), 2635, 2007: SEMIA 566 isolated from North American inoculant in 1966 and used in Brazilian commercial inoculants from 1966 to 1978, SEMIA 586 originally isolated in Maryland, USA, in 1961 but received from Australia in 1966 and used in Brazilian inoculants in 1977 (CB 1809, USDA 136, Nitragin 61A136, RCR 3407), SEMIA 5079 a natural variant of SEMIA 566 used in commercial inoculants since 1992 (CPAC 15; e. g. GELFIX 5 or ADHERE 60 from BASF Agricultural Specialties Ltd., Brazil), *B. japonicum* SEMIA 5080 a natural variant of SEMIA 586 used in commercial inoculants since 1992 (CPAC 7; e. g. GELFIX 5 or ADHERE 60 from BASF Agricultural Specialties Ltd., Brazil); *B. japonicum* TA-11 (TA11 NOD+) (NRRL B-18466; U.S. Pat. No. 5,021,076; Appl. Environ. Microbiol. 56, 2399-2403, 1990; e. g. VAULT® NP, from BASF Corp., USA), *B. japonicum* strains deposited at USDA known from U.S. Pat. No. 7,262,151 and Appl. Environ. Microbiol. 60, 940-94, 1994: USDA 3 isolated from *Glycine max* in Virginia (USA) in 1914, USDA 31 (=Nitragin 61A164) od Serogroup 31 isolated from *Glycine max* in Wisconsin (USA) in 1941, USDA 76 isolated from plant passage of strain USDA 74 (Serogroup 76) which has been isolated from *G. max* in California (USA) in 1956, USDA 110 (=IITA 2121, SEMIA 5032, RCR 3427, ARS 1-110 and Nitragin 61A89; Serogroup 110) isolated from *G. max* in Florida in 1959, USDA 121 isolated from *G. max* in Ohio (USA) in 1965 (Crop Science 26(5), 911-916, 1986); *B. japonicum* WB74 (e. g. Eco-Rhiz Soya from Plant Health Products (Pty) Ltd, South Africa; or Soybean inoculant from Stimuplant CC, South Africa), *B. lupini* LL13 isolated from *Lupinus iuteus* nodules from French soils (deposited at INRA, France; http://agriculture.gouv.fr/IMG/pdf/ch20060216.pdf), *B. lupini* strains from Australia and known from Palta J. A., Berger J. B. (eds), Proceed. 12$^{th}$ International Lupin Conference, 14-18 Sep. 2008, Fremantle, Western Australia, International Lupin Association, Canterbury, New Zealand, 47-50, http://www.lupins.org/pdf/conference/2008/Agronomy%20 and%20Production/John%20Howieson%20and%20G%20 OHara.pdf; Appl. Environ. Microbiol. 71, 7041-7052, 2005; Australian J. Exp. Agricult. 36(1), 63-70, 1996: strains WU425 isolated in Esperance, Western Australia from a non-Australian legume *Ornithopus compressus*, WSM471 isolated from *Ornithopus pinnatus* in Oyster Harbour, Western Australia, and WSM4024 isolated from lupins in Australia by CRS during a 2005 survey; *Burkholderia* sp. A396 (NRRL B-50319; WO 2013/032693; Marrone Bio Innovations, Inc., USA), *Candida oleophila* I-182 (NRRL Y-18846; Phytoparasitica 23(3), 231-234, 1995; e. g. Aspire® from Ecogen Inc., USA), *C. oleophila* strain O (NRRL Y-2317; Biological Control 51, 403-408, 2009), *Candida saitoana* (e. g. Biocure® [in mixture with lysozyme] and BioCoat® from Micro Flo Company, USA (BASF SE) and Arysta), chitosan (e. g. Armour-Zen® from BotriZen Ltd., NZ), *Clonostachys rosea f. catenulate* (also named *Gliocladium catenulatum*) J1446 isolated from Finnish field soil (NJF seminar No 389: Pest, disease and weed management in strawberry; Finland 8-9. Nov. 2006 in NJF Report 2(10), 15-15, 2006; DSM 9212; e. g. Primastop® or Prestop® from Verdera Oy, Finland), *Chromobacterium subtsugae* PRAA4-1 isolated from soil under an eastern hemlock (*Tsuga canadensis*) in the Catoctin Mountain region of central Maryland (NRRL B-30655; e. g. Grandevo® from Marrone Bio Innovations, USA), *Coniothyrium minitans* CON/M/91-08 (WO 1996/021358; DSM 9660; e. g. Contans® WG, Intercept® WG from Prophyta Biologischer Pflanzenschutz GmbH, Germany), *Cryphonectria parasitica* (hypovirulent strains; Microbiol. Reviews 56(4), 561-576, 1992; e. g. product Endothia parasitica from CNICM, France), *Cryptococcus albidus* (e. g. YIELD PLUS® from Anchor Bio-Technologies, South Africa), *Cryptophlebia leucotreta* granulovirus (CrleGV) (e. g. CRYPTEX from Adermatt Biocontrol, Switzerland), *Cydia pomonella* granulovirus (CpGV) V03 (DSM GV-0006; e. g. Madex® Max from Andermatt Biocontrol, Switzerland), CpGV V22 (DSM GV-0014; e. g. Madex® Twin from Adermatt Biocontrol, Switzerland), *Delftia acidovorans* RAY209 (ATCC PTA-4249; WO 2003/57861; e. g. BioBoost® from Brett Young, Winnipeg, Canada), *Dilophosphora alopecuri* (FarmNote 396, February 2010, Department of Agriculture and Food, Government of Western Australia; e.g. Twist Fungus from BASF Agricultural Specialties Pty Ltd, Australia), *Ecklonia maxima* (kelp) extract (J. Ecological Engineering 14(1), 48-52, 2013; e. g. KELPAK SL from Kelp Products Ltd, South Africa), *Flavobacterium* sp. H492 (ATCC B-505584; WO 2013/138398; e. g. MBI-302 from Marrone Bio Innovations, USA for soyean cyst nematode control), formononetin (U.S. Pat. No. 5,002,603; e. g. Myconate® from Plant Health Care plc, U.K.), *Fusarium oxysporum* Fo47 (non-pathogenic strain isolated from a suppressive soil located at Châteaurenard, France; Appl. Environ. Microbiol 68(8), 4044-4060, 2002; Fusaclean® from Natural Plant Protection, N.P.P. (société anonyme) Route d'Artix F-64150 Nogueres, France), *F. oxysporum* 251/2RB (Prevention Today Vol. 2, n. 1-2, 47-62, 2006; e. g. Biofox® C from S.I.A.P.A., Italy); *Glomus intraradices* (e. g. Myc® 4000 from ITHEC, France), *Glomus intraradices* RTI-801 (e. g. MYKOS from Xtreme Gardening, USA or RTI Reforestation Technologies International; USA), grapefruit seeds and pulp extract (e. g. BC-1000 from Chemie S.A., Chile), harpin (alpha-beta) protein (Science 257, 85-88, 1992; e. g. Messenger™ or HARP-N-Tek from Plant Health Care plc, U.K.), *Helicoverpa armigera* nucleopolyhedrovirus (HearNPV) (J. Invertebrate Pathol. 107, 112-126, 2011; e. g. Helicovex® from Adermatt Biocontrol, Switzerland), *Heterorhabditis bacteriophora* (e. g. Nemasys® G from BASF Agricultural Specialities Limited, UK), *Isaria fumosorosea* Apopka-97 (ATCC 20874; Biocontrol Science Technol. 22(7), 747-761, 2012; e. g. PFR-97™ or PreFeRal® from Certis LLC, USA), *I. fumosorosea* FE 9901 (ARSEF 4490; Biocontrol Science Technol. 22(7), 747-761, 2012; e. g. blastospores in NoFly™ WP from Natural Industries, Inc., Houston, Tex., USA or from Novozymes, U.S.A.), cis-jasmone (U.S. Pat. No. 6,890,525; U.S. Pat. No. 8,221,736; Plant Bioscience Limited, Norwich, U.K.), laminarin (e. g. in Vacciplant® from Laboratoires Goemar, St. Malo, France or Stahler SA, Switzerland), *Lecanicillium longisporum* KV42 and KV71 (e. g. Vertalec® from Koppert BV, Netherlands), *L. muscarium* Ve6 (also called KV01; IMI 19-79, CABI 268317, CBS 102071, ARSEF 5128; e. g. Mycotal® from Koppert BV, Netherlands), *Lysobacter antibioticus* 13-1 (Biological Control 45, 288-296, 2008), *L. antibioticus* HS124 (Curr. Microbiol. 59(6), 608-615, 2009), *L. enzymogenes* 3.1T8 (Microbiol. Res. 158, 107-115, 2003; Biological Control 31(2), 145-154, 2004); *Mesorhizobium* spp. strains known from Soil Biol. Biochem. 36(8), 1309-1317, 2004; Plant and Soil 348(1-2), 231-243, 2011: *M.* sp. WSM1271 collected in Sardinia, Italy, from plant host *Biserrula pelecinus, M.* sp. WSM 1497 collected in Mykonos, Greece, from *Biserrula pelecinus, Mesorhizobium ciceri* CC1192 collected in Israel from *Cicer arietinum* nodules (UPM 848, CECT 5549; Can. J. Microbiol. 48, 279-284, 2002; from Horticultural Research Station, Gosford, Australia), *M. huakuii* HN3015 isolated from *Astralagus sinicus* in a rice-growing field of Southern China (World J. Microbiol. Biotechn. 23(6), 845-851, 2007, ISSN 0959-3993), *M. loti* CC829 isolated from *L. ulginosus* nodules in USA (NZP 2012; commerical inoculant for *Lotus pedunculatus* and *L. ulginosus* in Australia), and *M. loti* SU343 isolated from host nodules in USA (commercial inoculant for *Lotus corniculatus* in Australia); *Metarhizium anisopliae* FI-1045 (AGAL V10/0104285; WO 2012/018266; e. g. Biocane® from BASF Agricultural Specialties Pty Ltd, Australia), *M. anisopliae* var. *anisopliae* F52 also called 275 or V275 (DSM 3884, ATCC 90448; e. g. Met52® Novozymes Biologicals BioAg Group, Canada), *M. anisopliae* ICIPE 69 isolated from a soil sample obtained from the Democratic Republic of Congo (DRC) and using the *Galleria* bait method in 1990 (e. g. Metathripol from ICIPE, Nairobe, Kenya), *M. anisopliae* var. *acridum* IMI 330189 isolated from *Ornithacris cavroisi* Niger (NRRL 50758; e. g. Green Muscle® from BASF Agricultural Specialities (Pty) Ltd., South Africa), *M. a.* var. *acridum* F1-985 isolated from a spur-throated locust, *Austracris guttulosa* (Walker), near Rockhampton, Queensland, Australia, in 1979 (ARSEF 324; Memoirs of the Entomological Society of Canada 171, 287-300, 1997; e. g. Green Guard® SC from BASF Agricultural Specialties Pty Ltd, Australia), *Metschnikowia fructicola* 277 isolated from the surface of grape berries (cv. Superior) grown in the central part of Israel (U.S. Pat. No. 6,994,849; NRRL Y-30752; e. g. Shemer® from Agrogreen, Israel, now distributed by Bayer CropSciences, Germany), *Microdochium dimerum* L13 (CNCM I-3141; e. g. Antibot® from Agrauxine, France), *Microsphaeropsis ochracea* P130A isolated from apple leaves from an abandoned orchard, St-Joseph-du-Lac, Quebec, Canada in 1993 (ATCC 74412; Mycologia 94(2), 297-301, 2002), *Muscodor albus* QST 20799 also called 620 originally isolated from the bark of a cinnamon tree in Honduras (NRRL 30547; e. g. Muscudor™ or QRD300 from AgraQuest, USA), *Muscodor albus* SA-13 (NRRL B-50774; US 2014/0086879 A1; e. g. MBI-601-EP from Marrone BioInnovations, Inc., USA), Neem oil (e. g. Trilogy®, Triact® 70 EC from Certis LLC, USA), *Nomuraea rileyi* strains SM6101, GU87401, SR86151, CG128 and VA9101 (Braz. Arch. Biol. Technol. 46(1), 13-19, 2003; WO 2013/110594), *Paecilomyces lilacinus* 251 isolated from infected nematode eggs in the Philippines (AGAL 89/030550; WO1991/02051; Crop Protection 27, 352-361, 2008; e. g. BioAct®/MeloCon® from Prophyta, Germany), *P. lilacinus* DSM 15169 (e. g. Nemata® SC from Live Systems Technology S.A., Colombia), *P. lilacinus* BCP2 (NRRL 50756; Acta agriculturae Slovenica, 101-2, 263-275, 2013; e. g. PL Gold from BASF Agricultural Specialities (Pty) Ltd., South Africa), *Paenibacillus alvei* NAS6G6 (WO 2014/029697; NRRL B-50755; e.g. BAC-UP from BASF Agricultural Specialities (Pty) Ltd., South Africa in mixture with *Bacillus pumilus* KFP9F), *P. polymyxa* PKB1 (ATCC 202127; Can. J. Microbiol. 48(2), 159-169, 2002), *Pantoea agglomerans* E325 (NRRL B-21856; Phytopathol. 101(10), 1234-41, 2011; Trees 26, 227-238, 2012; Bloomtime Biological™ from Northwest Agricultural Products, Inc., USA), *Pantoea vagans* (formerly *agglomerans*) C9-1 originally isolated in 1994 from apple stem tissue for control of fire blight in apple (J. Bacteriol. 192(24), 6486-6487, 2010; e. g. BlightBan C9-1® from NuFrams America Inc., USA), *Pasteuria* sp. ATCC PTA-9643 (WO 2010/085795), *Pasteuria* sp. Ph3 isolated from turfgrass soil samples collected at the DeBary Golf Course in central Florida (ATCC SD-5832; WO 2012/064527; for control of *Hoplolaimus galeatus* nematode from *Pasteuria* Bioscience, Inc. now Syngenta Crop Protection, LLC, USA), *Pasteuria* sp. Pr3 isolated from soil samples collected in the south-eastern United States (ATCC SD-5834; for control of *Rotylenchulus reniformis* nematode potentially of species *P. ramosa*; Naviva® ST from Syngenta Crop Protection, LLC, USA), *P. nishizawae* (WO 2010/80619), *P. nishizawae* Pn1 (Federal Register 76(22), 5808, Feb. 2, 2011; ATCC SD-5833; e.g. Clariva™ PN from Syngenta Crop Protection, LLC, USA), *P. penetrans* (U.S. Pat. No. 5,248,500; Del Monte Corp.), *P. ramosa* (WO 2010/080619), *P. thornea* (WO 2010/080619), *P. usgae* BL1 (ATCC SD-5835; J. Nematol. 42(2): 87-90, 2010; ibid. 43(2), 101-109, 2011; e. g. Econem™ for control of *Belonolaimus longicaudatus* from *Pasteuria* BioScience now Syngenta sold by Harell's LLC, Florida, USA for use on turf for management of *Belonolaimus longicaudatus*), *Penicillium bilaiae* (also called *P. bilaii*) strains ATCC 18309 (=ATCC 74319), ATCC 20851 and/or ATCC 22348 (=ATCC 74318) originally isolated from soil in southern Alberta (Fertilizer Res. 39, 97-103, 1994; Can. J. Plant Sci. 78(1), 91-102, 1998; U.S. Pat. No. 5,026,417, WO 1995/017806; e. g. Jump Start®, Provide® from Novozymes Biologicals BioAg Group, Canada), *P. bilaiae* NRRL 50162 and NRRL 50169 (WO 2010/037228), *Phlebiopsis gigantea* (e. g. RotStop® from Verdera Oy, Finland), *Pichia anomala* WRL-076 (NRRL Y-30842; U.S. Pat. No. 8,206,972), potassium bicarbonate (e. g. Amicarb® from Stähler SA, Switzerland), potassium silicate (e. g. Sil-MATRIX™ from Certis LLC, USA), *Pseudozyma flocculosa* PF-A22 UL (e. g. Sporodex® L from Plant Products Co. Ltd., Canada), *Pseudomonas* sp. Proradix (DSM 13134; WO 2001/40441, e. g. PRORADIX from Sourcon Padena GmbH & Co. KG, Hechinger Str. 262, 72072 Tübingen, Germany), *P. chloraphis* MA 342 (Microbiology Monographs 18, 21-43, 2011; e. g. Cerall® or Cedemon® from BioAgri AB, Uppsala, Sweden or Intrachem Bio Deutschland GmbH & Co. KG, Bad Camberg, Germany), *P. fluorescens* (e.g. in Bio Cure-B from T. Stanes & Company Limited, India; or in Blight-End from Agri Naturals, Mumbai, India), *P. fluorescens* A506 (Phytopathol 97(2), 244-249, 2007; ATCC 31948; e. g. BlightBan® from NuFarm Americas, Inc., Morrisville, N.C., USA), *P. fluorescens* ATCC 13525 of biovar I=biotype A; originally isolated from pre-filter tanks in England (DSM 50090; registered for use in Canada), *P. fluorescens* CHA0 (Mol. Plant Microbe Interact. 5(1), 4-13, 1992), *P. fluorescens* CL 145A (J. Invertebr. Pathol. 113(1), 104-14, 2013; e. g. Zequanox® from Marrone BioInnovations, Davis, Calif., USA), *P. fluorescens* NCIB 12089 (EP 0210734 A!; Victus® from Mauri Laboratories, 9 Moorebank Ave., Moorebank, NSW 2170, Australia), *P. fluorescens* Pf-5 isolated from root surface of cotton (ATCC BAA-477), *P. putida* ATCC 202153 (EMBRAPA 63/88 4 B; WO 2004/0245865), *Pythium oligandrum* DV 74 (US 2013/0035230; ATCC 38472; e. g. Poyversum® from Remeslo SSRO, Biopreparaty, Czech Rep. and from Gowan, USA), *Reynoutria sachalinensis* extract (EP 0307510 B1; e. g. Regalia® SC from Marrone BioInnovations, Davis, Calif., USA or Milsana® from BioFa AG, Germany), *Rhizobium leguminosarum* bv. *phaseoli* (e. g. RHIZO-STICK from BASF Corp., USA), *R. leguminosarum* bv. *phaseoli* RG-B10 (USDA 9041; from Int. J. Syst. Bacteriol. 46(1), 240-244, 1996; Int. J. Syst. Evol. Microbiol. 50, 159-170, 2000; e. g. Nodulator® Dry Bean in Africa, HiStick NT Dry bean in US, and Nodulator® Dry Bean in Canada from BASF Corp., USA, or BASF Agricultural Specialties Ltd., Canada), *R. l.* bv. *trifolii* CB782 (Nodulaid® peat for Kenya white clover from BASF Agricultural Specialties Pty Ltd, Australia), *R. l.* bv. *trifolii* CC275e (Nodulaid® peat for NZ white clover from BASF Agricultural Specialties Pty Ltd, Australia), *R. l.* bv. *trifolii* CC283b (ICMP 4073b; Proc. New Zealand Grassland Assoc. 56, 101-105, 1994; Microbiol. 153, 3184-3195, 2007; Nodulaid® peat for Caucasian clover from BASF Agricultural Specialties Pty Ltd, Australia), *R. l.* bv. *trifolii* CC1099 (Inoculating Legumes: A Practical Guide, ed. Grain Research and Development Corporation, 2012, ISBN 978-1-921779-45-9; e. g. Nodulaid® peat for sainfoin from BASF Agricultural Specialties Pty Ltd, Australia), *R. l.* bv. *trifolii* RP113-7 (Appl. Environ. Microbiol. 44(5), 1096-1101, 1982; e. g. Dormal® from BASF Corp., USA), *R. l.* bv. *trifolii* TA1 (Appl. Environ. Microbiol. 49(1), 127-131, 1985; e. g. Nodulaid® peat for white clover from BASF Agricultural Specialties Pty Ltd, Australia), *R. l.* bv. *trifolii* strain WSM1325 isolated in 1993 from the Greek Island of Serifos (Stand. Genomic Sci. 2(3), 347-356, 2010; Inoculating Legumes: A Practical Guide, ed. Grain Research and Development Corporation, 2012, ISBN 978-1-921779-45-9; Nodulaid® peat for sub clover and Nodulator® granules for sub clover both from BASF Agricultural Specialties Pty Ltd, Australia, for a broad range of annual clovers of Mediterranean origin), *R. l.* bv. *trifolii* strain WSM2304 isolated from *Trifolium polymorphum* in Uruguay in 1998 (Stand. Genomic Sci. 2(1), 66-76, 2010), *R. l.* bv. *viciae* P1NP3Cst being a Streptomycin-resistant mutant of P1NP3C isolated from pea root nodules in Bretenière, France (also referred to as 1435; New Phytol. 176, 680-690, 2007; ibid. 179(1), 224-235, 2008; e. g. Nodulator® PL Peat Granule from BASF Corp., USA; or Nodulator® XL PL from BASF Agricultural Specialties Ltd., Canada), *R. l.* bv. *viciae* RG-P2 also called P2 isolated from pea root nodules in Sakatchewan, Canada (e. g RhizUP peat for peas and lentils in Canada from BASF Agricultural Specialties Ltd., Canada), *R. l.* bv. *viciae* SU303 (e. g. Nodulaid® Group E from BASF Agricultural Specialties Pty Ltd, Australia), *R. l.* bv. *viciae* WSM1455 (e. g. Nodulaid® Group F from BASF Agricultural Specialties Pty Ltd, Australia), *R. tropici* CC511 (Agronomy, N.Z. 36, 4-35, 2006; e. g. Nodulaid® peat for common bean from BASF Agricultural Specialties Pty Ltd, Australia), *R. tropici* CIAT 899 isolated in Colombia (SEMIA 4077; Rev. Ciênc. Agron. 44(4) Fortaleza October/December 2013; e. g. Nitrafix® FEIJÃO peat for beans from BASF Agricultural Specialties Ltd., Brazil in mixture with strain SEMIA 4080), *R. tropici* H12 isolated in Planaltina, D F, Cerrados, Brazil (SEMIA 4088; Appl. Microbiol. Biotechnol. 93(5), 2035-49, 2012; e. g. Nitrafix® FEIJÃO from BASF Agricultural Specialties Ltd., Brazil), *R. tropici* PRF 81 isolated in Paraná, Brazil (SEMIA 4080; Soil Biology & Biochemistry 39, 867-876, 2007; BMC Microbiol. 12, 84, 2012; Nitrafix® FEIJÃO peat for beans from BASF Agricultural Specialties Ltd., Brazil in mixture with strain SEMIA 4077), *Sinorhizobium meliloti* RCR2011 also called 2011 or SU47 (MSDJ0848; Mol. Gen. Genomics 272, 1-17, 2004; e. g. Dormal® Alfalfa & Luzerne from BASF Corp., USA; Nitragin® Gold from Novozymes Biologicals BioAg Group, Canada), *Sphaerodes mycoparasitica* SMCD2220 also called SMCD2220-01 (I DAC 301008-01; WO 2011/022809), *Spodoptera littoralis* nucleopolyhedrovirus (SpliNPV) (e.g. in LITTOVIR from Adermatt Biocontrol, Switzerland), *Steinernema carpocapsae* (e. g. Millenium® from BASF Agricultural Specialities Limited, UK), *S. feltiae* (Nemashield® from BioWorks, Inc., USA; Nemasys® from BASF Agricultural Specialities Limited, UK), *S. kraussei* L137 (Nemasys® L from BASF Agricultural Specialities Limited, UK), *Streptomyces galbus* AQ6047 (NRRL 30232; WO 2012/135763; AgraQuest now Bayer CropScience LP, USA); *S. galbus* M1064 (NRRL 50334; WO 2012/135763; AgraQuest now Bayer CropScience LP, USA); *S. griseoviridis* K61 (Crop Protection 25, 468-475, 2006; e. g. Mycostop® from Verdera Oy, Espoo, Finland), *S. lydicus* WYEC 108 (U.S. Pat. No. 5,403,584; e. g. Actinovate® from Natural Industries, Inc., USA), *S. violaceusniger* YCED-9 (U.S. Pat. No. 5,968,503; e. g. DT-9® from Natural Industries, Inc., USA), *Talaromyces flavus* V117b isolated from soil (e. g. Protus® WG from Prophyta, Germany), and *Ulocladium oudemansii* HRU3 (Agronomy 3, 632-647, 2013; e. g. Botry-Zen® from Botry-Zen Ltd, NZ).

Strains can be obtained from culture collections and deposition centers (listed by their acronym=strain prefix here: http://www.wfcc.info/ccinfo/collection/by_acronym/) such as strains with prefices AGAL or NMI from: National Measurement Institute, 1/153 Bertie Street, Port Melbourne, Victoria, Australia 3207; ATCC: American Type Culture Collection, 10801 University Blvd., Manassas, Va. 20110-2209, USA; BR: Embrapa Agrobiology Diazothrophic Microbial Culture Collection, P.O.Box 74.505, Seropedica, Rio de Janeiro, 23.851-970, Brazil; CABI or IMI: CABI Europe—International Mycological Institute, Bakeham Lane, Egham, Surrey, TW20 9TYNRRL, UK; CB: The CB *Rhizobium* Collection, School of Environment and Agriculture, University of Western Sydney, Hawkesbury, Locked Bag 1797, South Penrith Distribution Centre, NSW 1797, Australia; CBS: Centraalbureau voor Schimmelcultures, Fungal Biodiversity Centre, Uppsalaan 8, PO Box 85167, 3508 AD Utrecht, Netherlands; CC: Division of Plant Industry, CSIRO, Canberra, Australia; CNCM: Collection Nationale de Cultures de Microorganismes, Institute Pasteur, 25 rue du Docteur Roux, F-75724 PARIS Cedex 15; CPAC: Embrapa-Cerrados, CX. Postal 08223, Planaltina, DF, 73301-970, Brazil; DSM: Leibniz-Institut DSMZ-Deutsche Sammlung von Mikroorganismen und Zellkulturen GmbH, Inhoffenstraβe 7 B, 38124 Braunschweig, Germany; IDAC: International Depositary Authority of Canada Collection, Canada; ICMP: Interntional Collection of Micro-organisms from Plants, Landcare Research, Private Bag 92170, Auckland Mail Centre, Auckland 1142, New Zealand; IITA: IITA, PMB 5320, Ibadan, Nigeria; INTA: Agriculture Collection Laboratory of the Instituto de Microbiologia y Zoologia Agricola (IMYZA), Instituto Nacional de Tecnologi'a Agropecuaria (INTA), Castelar, Argentina; MSDJ: Laboratoire de Microbiologie des Sols, INRA, Dijon, France; MUCL: Mycothèque de l'Université catholique de Louvain, Croix du Sud 2, box L7.05.06, 1348 Louvain-la-Neuve, Belgium; NCIMB or NICB: The National Collections of Industrial and Marine Bacteria Ltd., Torry Research Station, P.O. Box 31, 135 Abbey Road, Aberdeen, AB9 8DG, Scotland; Nitragin: Nitragin strain collection, The Nitragin Company, Milwaukee, Wis., USA, NRRL or ARSEF (collection of entomopathogenic fungi): ARS Culture Collection of the National Center for Agricultural Utilization Research, Agricultural Research Service, U.S. Department of Agriculture, 1815 North University Street, Peoria, Ill. 61604, USA; NZP: Department of Scientific and Industrial Research Culture Collection, Applied Biochemistry Division, Palmerston North, New Zealand; PPRI: ARC-Plant Protection Research Institute, Private Bag X134, Queenswood Pretoria, Gauteng, 0121, South Africa; SEMIA: FEPAGRO-Fundação Estadual de Pesquisa Agropecuária, Rua Gonçalves Dias, 570, Bairro Menino Deus, Porto Alegre/RS, Brazil; SRDI: SARDI, Adelaide, South Australia; USDA: U.S. Department of Agriculture, Agricultural Research Service, Soybean and Alfalfa Research Laboratory, BARC-West, 10300 Baltimore Boulevard, Building 011, Beltsville, Md. 20705, USA (Beltsville Rhiz. Cult. Catalog: http://pdf.usaid.gov/pdf_docs/PNAAW891.pdf); and WSM: Murdoch University, Perth, Western Australia. Further strains may be found at: http://gcm.wfcc.info/; http://www.landcareresearch.co.nz/resources. collections/icmp.

Jasmonic acid, its salts (jasmonates) or derivatives include without limitation potassium, sodium, lithium, ammonium, dimethylammonium, isopropylammonium, diolammonium and diethtriethanolammonium jasmonate; and also jasmonic acid methyl ester, jasmonic acid amide, jasmonic acid methylamide, jasmonic acid-L-amino acid (amide-linked) conjugates (e. g. conjugates with L-isoleucine, L-valine, L-leucine, or L-phenylalanine), 12-oxo-phytodienoic acid, coronatine, coronalon, coronafacoyl-L-serine, coronafacoyl-L-threonine, methyl esters of 1-oxo-indanoyl-isoleucine, methyl esters of 1-oxo-indanoyl-leucine, cis-jasmone, linoleic acid or derivatives thereof, and combinations of any of the above.

Humates are humic and fulvic acids extracted from a form of lignite coal and clay, known as leonardite. Humic acids are organic acids that occur in humus and other organically derived materials such as peat and certain soft coal. They have been shown to increase fertilizer efficiency in phosphate and micro-nutrient uptake by plants as well as aiding in the development of plant root systems.

According to one embodiment of the inventive mixtures, the at least one pesticide II is selected from the groups L1) to L6):

L1) Microbial pesticides with fungicidal, bactericidal, viricidal and/or plant defense activator activity selected from: *Ampelomyces quisqualis* M-10 (L.1.1), *Aspergillus flavus* NRRL 21882 (L1.2), *Aureobasidium pullulans* DSM 14940 (L1.3), *A. pullulans* DSM 14941 (L.1.4), *Bacillus altitudinis* 41KF2b (L.1.5), *B. amyloliquefaciens* IN937a (L.1.11), *B. amyloliquefaciens* IT-45 (L.1.12), *B. amyloliquefaciens* ssp. *plantarum* D747 (L.1.13), *B. amyloliquefaciens* ssp. *plantarum* FZB24 (L.1.14), *B. amyloliquefaciens* ssp. *plantarum* FZB42 (L.1.15), *B. amyloliquefaciens* ssp. *plantarum* GB03 (L.1.16), *B. amyloliquefaciens* ssp. MBI600 (NRRL B-50595) (L.1.17), *B. amyloliquefaciens* ssp. *plantarum* QST-713 (L.1.18), *B. mycoides* AQ726 (L.1.21), *B. mycoides* strain J (L.1.22), *B. pumilus* INR-7 (L.1.23), *B. pumilus* KFP9F (L.1.24), *B. pumilus* QST 2808 (L.1.25), *B. pumilus* GHA 180 (L.1.26), *B. simplex* ABU 288 (L.1.27), *B. subtilis* CX-9060 (L.1.29), *B. subtilis* FB17 (L.1.30), *B. subtilis* GB07 (L.1.31), *Candida oleophila* I-82 (L.1.32), *C. oleophila* O (L.1.33), *C. saitoana* (L.1.34), *Clavibacter michiganensis* (bacteriophages) (L.1.35), *Coniothyrium minitans* CON/M/91-08 (L.1.36), *Cryphonectria parasitica* (L.1.37), *Cryptococcus albidus* (L.1.38), *Dilophosphora alopecuri* (L.1.39), *Fusarium oxysporum* (L.1.40), *Clonostachys rosea f. catenulata* J1446 (L.1.41), *Gliocladium roseum* 321U (L.1.42), *Metschnikowia fructicola* NRRL Y-30752 (L.1.43), *Microdochium dimerum* (L.1.44), *Microsphaeropsis ochracea* P130A (L.1.45), *Muscodor albus* QST 20799 (L.1.46), *Muscodor albus* SA-13 (L.1.47), *Paenibacillus alvei* NAS6G6 (L.1.48), *Paenibacillus polymyxa* PKB1 (L.1.49), *Pantoea agglomerans* E325 (L.1.90), *Pantoea vagans* C9-1 (L.1.50), *Penicillium bilaiae*-ATCC 22348 (L.1.51), *P. bilaiae* ATCC 20851 (L.1.52), *Penicillium bilaiae* ATCC 18309 (L.1.53), *Phlebiopsis gigantea* (L.1.54), *Pichia anomala* WRL-76 (L.1.55), *Pseudomonas* sp. Proradix (L.1.56), *Pseudomonas chloraphis* MA 342 (L.1.57), *P. fluorescens* A506 (L.1.58), *P. fluorescens* CL 145A (L.1.91), *P. fluorescens* NCIB 12089 (L.1.92), *P. fluorescens* Pf-5 (L.1.93), *P. fluorescens* WCS 374 (L.1.94), *P. fluorescens* ATCC 13525 (L.1.95), *P. fluorescens* CHA0 (L.1.96), *P. putida* ATCC 202153 (L.1.97), *Pseudozyma flocculosa* PF-A22 UL (L.1.59), *Pythium oligandrum* DV 74 (L.1.60), *Sphaerodes mycoparasitica* SMCD2220 (L.1.61), *Streptomyces griseoviridis* K61 (L.1.62), *S. lydicus* WYEC 108 (L.1.63), *S. violaceusniger* XL-2 (L.1.64), *S. violaceusniger* YCED-9 (L.1.65), *Talaromyces flavus* V117b (L.1.66), *Typhula phacorrhiza* 94671 (L.1.86), *Ulocladium oudemansii* H RU3 (L.1.87), *Verticillium dahlia* (L.1.88), zucchini yellow mosaic virus (avirulent strain) (L.1.89);

L2) Biochemical pesticides with fungicidal, bactericidal, viricidal and/or plant defense activator activity selected from: chitosan (hydrolysate) (L.2.1), harpin protein (L.2.2), laminarin (L.2.3), Menhaden fish oil (L.2.4), natamycin (L.2.5), Plum pox virus coat protein (L.2.6), potassium bicarbonate (L.2.7), *Reynoutria sachalinensis* extract (L.2.8), salicylic acid (L.2.9), potassium or sodium bicarbonate (L.2.10), tea tree oil (L.2.11);

L3) Microbial pesticides with insecticidal, acaricidal, molluscidal and/or nematicidal activity selected from: *Agrobacterium radiobacter* K1026 (L.3.1), *A. radiobacter* K84 (L.3.2), *Bacillus firmus* I-1582 (L.3.3); *B. thuringiensis* ssp. *aizawai* strains: ABTS-1857 (L.3.4), SAN 401 I (L.3.5), ABG-6305 (L.3.6) and ABG-6346 (L.3.7); *B. t.* ssp. *israelensis* AM65-52 (L.3.8), *B. t.* ssp. *israelensis* SUM-6218 (L.3.9), *B. t.* ssp. *galleriae* SDS-502 (L.3.10), *B. t.* ssp. *kurstaki* EG 2348 (L.3.11), *B. t.* ssp. *kurstaki* SB4 (L.3.12), *B. t.* ssp. *kurstaki* ABTS-351 (HD-1) (L.3.13), *Beauveria bassiana* ATCC 74040 (L.3.14), *B. bassiana* GHA (L.3.15), *B. bassiana* H123 (L.3.16), *B. bassiana* DSM 12256 (L.3.17), *B. bassiana* PPRI 5339 (L.3.18), *B. brongniartii* (L.3.19), *Burkholderia* sp. A396 (L.3.20), *Chromobacterium subtsugae* PRAA4-1 (L.3.21), *Cydia pomonella* granulosis virus V22 (L.3.22), *Cydia pomonella* granulosis virus V1 (L.3.23), *Cryptophlebia leucotreta* granulovirus (CrleGV) (L.3.57), *Flavobacterium* sp. H492 (L.3.60), *Helicoverpa armigera* nucleopolyhedrovirus (HearNPV) (L.3.58), *Isaria fumosorosea* Apopka-97 (L.3.24), *Lecanialium longisporum* KV42 (L.3.25), *L. longisporum* KV71 (L.3.26), *L. muscarium* KV01 (L.3.27), *Metarhizium anisopliae* FI-985 (L.3.28), *M. anisopliae* FI-1045 (L.3.29), *M. anisopliae* F52 (L.3.30), *M. anisopliae* ICIPE 69 (L.3.31), *M. anisopliae* var. *acridum* IMI 330189 (L.3.32); *Nomuraea rileyi* strains: SA86101 (L.3.33), GU87401 (L.3.34), SR86151 (L.3.35), CG128 (L.3.36) and VA9101 (L.3.37); *Paecilomyces fumosoroseus* FE 9901 (L.3.38), *P. lilacinus* 251 (L.3.39), *P. lilacinus* DSM 15169 (L.3.40), *P. lilacinus* BCP2 (L.3.41), *Paembacillus popilliae* Dutky-1940 (NRRL B-2309=ATCC 14706) (L.3.42), *P. popilliae* Dutky 1 (L.3.43), *P. popilliae* KLN 3 (L.3.56), *Pasteuria* sp. Ph3 (L.3.44), *Pasteuria* sp. ATCC PTA-9643 (L.3.45), *Pasteuria* sp. ATCC SD-5832 (L.3.46), *P. nishizawae* Pn1 (L.3.46), *P. penetrans* (L.3.47), *P. ramosa* (L.3.48), *P.* sp. Pr-3 (L.3.49), *P. thornea* (L.3.50), *P. usgae* (L.3.51), *Pseudomonas fluorescens* CL 145A (L.3.52), *Spodoptera littoralis* nucleopolyhedrovirus (SpliNPV) (L.3.59), *Steinernema carpocapsae* (L.3.53), *S. feltiae* (L.3.54), *S. kraussei* L137 (L.3.55);

L4) Biochemical pesticides with insecticidal, acaricidal, molluscidal, pheromone and/or nematicidal activity selected from: L-carvone (L.4.1), citral (L.4.2), (E,Z)-7,9-dodecadien-1-yl acetate (L.4.3), ethyl formate (L.4.4), (E,Z)-2,4-ethyl decadienoate (pear ester) (L.4.5), (Z,Z,E)-7,11,13-hexadecatrienal (L.4.6), heptyl butyrate (L.4.7), isopropyl myristate (L.4.8), cis-jasmone (L.4.9), lavanulyl senecioate (L.4.10), 2-methyl 1-butanol (L.4.11), methyl eugenol (L.4.12), methyl jasmonate (L.4.13), (E,Z)-2,13-octadecadien-1-ol (L.4.14), (E,Z)-2,13-octadecadien-1-ol acetate (L.4.15), (E,Z)-3,13-octadecadien-1-ol (L.4.16), R-1-octen-3-ol (L.4.17), pentatermanone (L.4.18), potassium silicate (L.4.19), sorbitol actanoate (L.4.20), (E,Z,Z)-3,8,11-tetradecatrienyl acetate (L.4.21), (Z,E)-9,12-tetradecadien-1-yl acetate (L.4.22), Z-7-tetradecen-2-one (L.4.23), Z-9-tetradecen-1-yl acetate (L.4.24), Z-11-tetradecenal (L.4.25), Z-11-tetradecen-1-ol (L.4.26), *Acacia negra* extract (L.4.27), extract of grapefruit seeds and pulp (L.4.28), extract of *Chenopodium ambrosioides* (L.4.29), Catnip oil (L.4.30), Neem oil (L.4.31), Quillay extract (L.4.32), Tagetes oil (L.4.33);

L5) Microbial pesticides with plant stress reducing, plant growth regulator, plant growth promoting and/or yield enhancing activity selected from: *Azospirillum amazonense* BR 11140 (SpY2) (L.5.1), *A. brasilense* Ab-V5 (L.5.74), *A. brasilense* Ab-V6 (L.5.75), *A. brasilense* AZ39 (L.5.2), *A. brasilense* XOH (L.5.3), *A. brasilense* Sp245 (BR 11005) (L.5.4), *A. brasilense* BR 11002 (L.5.5), *A. lipoferum* BR 11646 (Sp31) (L.5.6), *A. irakense* (L.5.7), *A. halopraeferens* (L.5.8), *Bradyrhizobium* sp. PNL01 (L.5.9), *B.* sp. (*Arachis*) CB1015 (L.5.10), *B.* sp. (*Arachis*) USDA 3446 (L.5.11), *B.* sp. (*Arachis*) SEMIA 6144 (L.5.12), *B.* sp. (*Arachis*) SEMIA 6462 (L.5.13), *B.* sp. (*Arachis*) SEMIA 6464 (L.5.14), *B.* sp. (*Vigna*) (L.5.15), *B. elkanii* SEMIA 587 (L.5.16), *B. elkanii* SEMIA 5019 (L.5.17), *B. elkanii* U-1301 (L.5.18), *B. elkanii* U-1302 (L.5.19), *B. elkanii* USDA 74 (L.5.20), *B. elkanii* USDA 76 (L.5.21), *B. elkanii* USDA 94 (L.5.22), *B. elkanii* USDA 3254 (L.5.23), *B. japonicum* 532c (L.5.24), *B. japonicum* CPAC 15 (L.5.25), *B. japonicum* E-109 (L.5.26), *B. japonicum* G49 (L.5.27), *B. japonicum* TA-11 (L.5.28), *B. japonicum* USDA 3 (L.5.29), *B. japonicum* USDA 31 (L.5.30), *B. japonicum* USDA 76 (L.5.31), *B. japonicum* USDA 110 (L.5.32), *B. japonicum* USDA 121 (L.5.33), *B. japonicum* USDA 123 (L.5.34), *B. japonicum* USDA 136 (L.5.35), *B. japonicum* SEMIA 566 (L.5.36), *B. japonicum* SEMIA 5079 (L.5.37), *B. japonicum* SEMIA 5080 (L.5.38), *B. japonicum* WB74 (L.5.39), *B. liaoningense* (L.5.40), *B. lupini* LL13 (L.5.41), *B. lupini* WU425 (L.5.42), *B. lupini* WSM471 (L.5.43), *B. lupini* WSM4024 (L.5.44), *Glomus intraradices* RTI-801 (L.5.45), *Mesorhizobium* sp. WSM1271 (L.5.46), *M.* sp. WSM1497 (L.5.47), *M. ciceri* CC1192 (L.5.48), *M. huakii* (L.5.49), *M. loti* CC829 (L.5.50), *M. loti* SU343 (L.5.51), *Rhizobium leguminosarum* bv. *phaseoli* RG-B10 (L.5.52), *R. l.* bv. *trifolii* RP113-7 (L.5.53), *R. l.* bv. *trifolii* 095 (L.5.57), *R. l.* bv. *trifolii* TA1 (L.5.58), *R. l.* bv. *trifolii* CC283b (L.5.59), *R. l.* bv. *trifolii* CC275e (L.5.60), *R. l.* bv. *trifolii* CB782(L.5.61), *R. l.* bv. *trifolii* CC1099 (L.5.62), *R. l.* bv. *trifolii* WSM1325 (L.5.63), *R. l.* bv. *viciae* SU303 (L.5.64), *R. l.* bv. *viciae* WSM1455 (L.5.65), *R. l.* bv. *viciae* P1NP3Cst (L.5.66), *R. l.* bv. *viciae* RG-P2 (L.5.67), *R. tropici* PRF 81 (L.5.68), *R. tropici* SEMIA 4077 (L.5.69), *R. tropici* CC511(L.5.70), *Sinorhizobium meliloti* RCR2011 (L.5.71), *S. meliloti* NRG185 (L.5.72), *S. meliloti* RRI128 (L.5.73);

L6) Biochemical pesticides with plant stress reducing, plant growth regulator and/or plant yield enhancing activity selected from: abscisic acid (L.6.1), aluminium silicate (kaolin) (L.6.2), 3-decen-2-one (L.6.3), formononectin (L.6.4), genistein (L.6.5), hesperetin (L.6.6), homobrassinolide (L.6.7), humates (L.6.8), methyl jasmonate (L.6.9), cis-jasmone (L.6.10), lysophosphatidyl ethanlamine (L.6.11), naringenin (L.6.12), polymeric polyhydroxy acid (L.6.13), salicylic acid (L.6.14), *Ascophyllum nodosum* (Norwegian kelp, Brown kelp) extract (L.6.15) and *Ecklonia maxima* (kelp) extract (L.6.16).

The present invention furthermore relates to agrochemical compositions comprising a mixture of at least one microorganism I (component 1) and at least one biopesticide selected from the group L) (component 2), in particular at least one further fungicidal biopesticide selected from the groups L1) and L2), as described above, and if desired at least one suitable auxiliary.

Preference is also given to mixtures comprising as pesticide II (component 2) a biopesticide from group L1), preferably selected from *Bacillus amyloliquefaciens* herein even more preferably from strains IN937a, IT-45; *B. amyloliquefaciens* ssp. *plantarum* (formerly called *B. subtilis* or *B. subtilis* spp. *amyloliquefaciens*) herein even more preferably from strains MBI600, D747, FZB254, FZB42, GB03, and QST-713; *B. pumilus* herein even more preferably from strains GHA 180, INR-7, KFP9F and QST 2808; *B. simplex* herein more preferably strain ABU 288; *B. solisalsi*; *B. subtilis* herein even more preferably selected from strains CX-9060, FB17 and GB07; *Muscodor albus* herein more preferably strains QST 20799 and SA-13; *Paenibacillus alvei* herein more preferably strain NAS6G6, *Paenibacillus polymyxa* herein more preferably strain PKB1, *Penicillium bilaiae* herein more preferably strains ATCC 22348, ATCC 20581 and ATCC 18309; *Pseudomonas fluorescens* herein more preferably strain A506; *Sphaerodes mycoparasitica* herein more preferably strain SMCD2220.

Preference is also given to mixtures comprising as pesticide II (component 2) a biopesticide from group L1), even more preferably selected from even more preferably from *B. amyloliquefaciens* ssp. *plantarum* M B1600, *B. amyloliquefaciens* ssp. *plantarum* QST-713, *B. pumilus* INR-7, *B. pumilus* QST 2808, *B. simplex* ABU 288, *B. subtilis* FB17, and *Paenibacillus alvei* NAS6G6.

According to one embodiment of the inventive mixtures, the at least one pesticide II is *Bacillus amyloliquefaciens* ssp. *plantarum* MBI600. These mixtures are particularly suitable in soybean.

According to another embodiment of the inventive mixtures, the at least one pesticide II is *B. pumilus* INR-7. These mixtures are particularly suitable in soybean and corn.

According to a further embodiment, the at least one pesticide II is *Bacillus simplex*, preferably *B. simplex* ABU 288. These mixtures are particularly suitable in soybean and corn.

According to a further embodiment, the at least one pesticide II is *Bacillus subtilis*, preferably *B. subtilis* strain FB17.

According to one embodiment of the inventive mixtures, the at least one pesticide II is selected from *Bacillus amyloliquefaciens* spp. *plantarum* FZB24, *B. amyloliquefaciens* ssp. *plantarum* FZB42, *B. amyloliquefaciens* ssp.

plantarum D747, *B. amyloliquefaciens* ssp. *plantarum* MBI600, *B. amyloliquefaciens* spp. *plantarum* GB03, *B. amyloliquefaciens* spp. *plantarum* QST-713, *B. pumilus* GB34, *B. pumilus* INR-7, *B. pumilus* KFP9F, *B. pumilus* QST 2808, *B. pumilus* GHA 180, *B. simplex* ABU 288, *B. subtilis* CX-9060, *B. subtilis* FB17 and B. *subtilis* GB07. These mixtures are particularly suitable in soybean and corn, in particular for seed treatment.

According to one embodiment of the inventive mixtures, the at least one pesticide II is *Coniothyrium minitans* CON/M/91-08. These mixtures are particularly suitable for seed and/or soil treatment.

According to a further embodiment, the at least one pesticide II is selected from *Pseudomonas* spp., preferably selected from *P. chloraphis* herein more preferably strain MA 342 and *Pseudomonas* sp. DSM 13134; *P. fluorescens* herein more preferably selected from strains A506, WCS 374 and Pf-5; and *P. putida* herein more preferably strain ATCC 202153.

The present invention also relates to mixtures wherein the at least one pesticide II is selected from the fungal species *Muscodor albus* preferably from the strains SA-13 and QST 20799, which are particularly suiable for soil and seed treatment against soil-borne pathogens and/or nematodes.

Preference is also given to mixtures comprising as pesticide II (component 2) a biopesticide from group L2), preferably selected from chitosan (hydrolysate), methyl-jasmonate, cis-jasmone, laminarin, *Reynoutria sachalinensis* extract and tea tree oil; even more preferable from methyl jasmonate and cis-jasmone.

Preference is also given to mixtures comprising as pesticide II (component 2) a biopesticide from group L3), preferably selected from *Agrobacterium radiobacter* herein preferably strain K1026, *Bacillus firmus* herein referably strain I-1582, *Bacillus thuringiensis* ssp. *kurstaki* herein preferably strain SB4, *Beauveria bassiana* herein preferably selected from strains GHA, H123, DSM 12256 and PPRI 5339; *Burkholderia* sp. and herein preferably strain A396, *Metarhizium anisopliae* var. *acridum* herein preferably strain IMI 330189, *M. anisopliae* herein preferably selected from strains FI-985, FI-1045, F52 and ICIPE 69; *Paecilomyces lilacinus* herein preferably selected from strains 251, DSM 15169 and BCP2, *Paenibacillus popilliae* herein preferably selected from strains Dutky-1940, KLN 3 and Dutky 1; *Pasteuria nishazawa* and herein preferably strain Pn1.

Preference is also given to mixtures comprising as pesticide II (component 2) a biopesticide from group L3), even more preferably from *Bacillus thuringiensis* ssp. *kurstaki* SB4, *B. bassiana* DSM 12256, *B. bassiana* PPRI 5339, *Paecilomyces lilacinus* DSM 15169, *P. lilacinus* BCP2, *P. lilacinus* 251, *Paenibacillus popilliae* Dutky-1940, *P. popilliae* KLN 3 and *P. popilliae* Dutky 1.

According to a further embodiment, the at least one pesticide II is *Beauveria bassiana* PPRI 5339.

According to a further embodiment, the at least one pesticide II is *Bacillus firmus*, preferably spores of strain CNCM I-1582, preferably useful for seed treatment of soybean and corn against nematodes and insects.

According to a further embodiment, the at least one pesticide II is *Bacillus cereus*, preferably spores of CNCM I-1562, preferably useful for seed treatment of soybean and corn against nematodes and insects.

According to a further embodiment, the at least one pesticide II is a mixture of spores of *B. firmus* and *B. cereus*, preferably mixtures spores of above mentioned strains CNCM I-1582 and CNCM I-1562, preferably useful for seed treatment of soybean and corn against nematodes and insects.

According to a further embodiment, the at least one pesticide II is selected from *Bacillus t.* ssp. *kurstaki* preferably from strains EG 2348, SB4 and ABTS-351 (HD-1), in particular *B. t.* ssp. *kurstaki* SB4. These strains are used for control of lepidopteran larvae, but without noctuidae.

According to one embodiment of the inventive mixtures, the at least one pesticide II is selected from *Bacillus firmus* CNCM I-1582, *Paecilomyces lilcinus* 251, *Pasteuria nishizawa* Pn1 and *Burkholderia* sp. A396 having nematicidal, acaricidal and/or insecticidal activity. These mixtures are particularly suitable in soybean and corn, in particular for seed treatment.

Preference is also given to mixtures comprising as pesticide II (component 2) a biopesticide from group L4), preferably selected from methyl jasmonate, *Acacia negra* extract, extract of grapefruit seeds and pulp, Catnip oil, Neem oil, Quillay extract and Tagetes oil, in particular methyl jasmonate or water-based Quillay extract.

Preference is also given to mixtures comprising as pesticide II (component 2) a biopesticide from group L5), preferably selected from *Azospialum amazonense, A. brasllense, A. lipoferum, A. irakense, A. halopraeferens, Bradyrhizobium* sp. (*Vigna*), *B. elkanil; B. japonicum Paembacillus alvei, Penicilium bilaiae, Rhizobium legu*minosarum bv. *phaseoli; R. I.* bv. *trifolii, R. I.* bv. *viciae*, and *Sinorhizobium meliloti*.

Preference is also given to mixtures comprising as pesticide II (component 2) a biopesticide from group L5) selectedifrom *Azospialum amazonense* SpY2$^T$, *A. brasllense* XOH, *A. brasilense* Sp245, *A. brasilense* Cd, *A. brasllense* Ab-V5, *A. brasilense* Ab-V6, *A. lipoferum* Sp31, *Bradyrhizobium* sp. (*Vigna*) PNL1, *B. elkanii* SEMIA 587, *B. elkanii* SEMIA 5019, *B. japonicum* SEMIA 5079, *B. japonicum* SEMIA 5080, *B. japonicum* TA-11, *B. japonicum* 532c, *Paembacillus alvei* NAS6G6, *Peniciillium bilaiae* strains ATCC 18309, ATCC 20851 and ATCC 22348; *Rhizobium leguminosarum* bv. *phaseoli* P1NP3Cst, *R. I.* bv. *phaseoli* RG-B10, *R. I.* bv. *trifolii* RP113-7, *R. I.* bv. *viciae* SU303, *R. I.* bv. *viciae* WSM1455, *R. tropici* SEMIA 4077, *R. tropici* PRF 81 and *Sinorhizobium meliloti*, even more preferably selected from *Azospirillum brasilense* Sp245, *Bradyrhizobium* sp. (*Vigna*) PNL1, *B. elkanii* SEMIA 587, *B. elkanii* SEMIA 5019, *B. japonicum* SEMIA 5079, *B. japonicum* SEMIA 5080, *B. japonicum* TA-11 and *B. japonicum* 532c.

According to a further embodiment, component 2) in the mixtures comprises at least one biopesticide II strain selected from *Azospirillum brasilense* Sp 245, *A. brasilense* Ab-V5, *A. brasilense* Ab-V6, *Bradyrhizobium elkanii* SEMIA 5019, *B. elkanii* SEMIA 587, *B. japonicum* 532c, *B. japonicum* E-109, *B. japonicum* SEMIA 5079 and *B. japonicum* SEMIA 5080.

The present invention also relates to mixtures, wherein the at least one pesticide II is selected from *B. japonicum* and *B. elkanii* and further comprises a pesticide III, wherein pesticide III is selected from jasmonic acid, its salts and derivatives thereof, preferably methyl-jasmonate or cis-jasmone.

The present invention also relates to mixtures wherein the at least one pesticide II is selected from *Bacillus amyloliquefaciens* ssp. *plantarum* M B1600, *B. amyloliquefaciens* ssp. *plantarum* FZB24, *B. amyloliquefaciens* ssp. *plantarum* FZB42, *B. amyloliquefaciens* ssp. *plantarum* D747, *B. amyloliquefaciens* ssp. *plantarum* QST-713, *B. firmus* CNCM I-1582, *B. pumilus* GHA 180, *B. pumilus* INR-7, *B.*

*pumilus* QST 2808, *B. simplex* ABU 288, *B. subtilis* FB17, *Burkholderia* sp. A396, *Coniothyrium minitans* CON/M/91-08, *Paecilomyces lilacinus* 251, *Paenibacillus alvei* NAS6G6, *Pasteuria nishizawae* Pn1, *P. bilaiae* ATCC 18309, *P. bilaiae* ATCC 20851, *P. bilaiae* ATCC 22348; cis-jasmone, methyl jasmonate and harpin protein The pesticides II of chemical nature (chemical pesticides) are described by common names, their preparation and their activity against pests is known (cf.: http://www.alanwood.net/pesticides/); these pesticides are often commercially available.

Preference is also given to mixtures comprising as component 2) at least one pesticide II from the groups A) to H), N) and O) selected from:
- A) Inhibitors of complex III at $Q_o$ site selected from: pyraclostrobin, azoxystrobin, picoxystrobin, trifloxystrobin, dimoxystrobin, enestroburin, fenaminstrobin, fluoxastrobin, kresoxim-methyl, mandestrobine, metominostrobin, orysastrobin, pyrametostrobin, pyraoxystrobin;
  - inhibitors of complex II selected from: fluxapyroxad, boscalid, benzovindiflupyr, penflufen, penthiopyrad, sedaxane, fluopyram, bixafen, flutolanil, isofetamid, isopyrazam; carboxin, benodanil, fenfuram, flutolanil, furametpyr, mepronil, oxycarboxin, thifluzamide; other respiration inhibitor: silthiofam;
- B) DMI fungicides selected from: ipconazole, difenoconazole, prothioconazole, prochloraz, triticonazole, flutriafol, cyproconazole, diniconazole, diniconazole-M, fluquinconazole, flusilazole, hexaconazole, imazalil, imibenconazole, metconazole, myclobutanil, simeconazole, tebuconazole, triadimenol, uniconazole;
- C) Nucleic acid synthesis inhibitors selected from: metalaxyl, mefenoxam;
- D) Inhibitors of cell division and cytoskeleton selected from: thiabendazole, thiophanate-methyl, carbendazim; ethaboxam;
- F) MAP/histidine kinase inhibitor: fludioxonil;
- G) Lipid and membrane synthesis inhibitors selected from: dimethomorph, zoxamide, flumorph, mandipropamid, pyrimorph, benthiavalicarb, iprovalicarb, oxathiapiprolin, valifenalate;
- H) Inhibitors with Multi Site Action selected from: thiram, ziram;
- N) Herbicides selected from: glyphosate and dicamba;
- O) Insecticides selected from:
  - organo(thio)phosphates selected from: acephate, chlorpyrifos,
  - carbamates selected from: methiocarb, thiodicarb;
  - pyrethroids selected from: tefluthrin, bifenthrin, cypermethrin, alpha-cypermethrin, cyfluthrin, beta-cyfluthrin, lambda-cyhalothrin, deltamethrin, esfenvalerate, etofenprox, fenvalerate, flucythrinate, permethrin;
  - macrocyclic lactone insecticides selected from: abamectin, spinosad;
  - nicotinic receptor agonists/antagonists compounds selected from: clothianidin, imidacloprid, thiamethoxam, dinotefuran, acetamiprid, flupyradifurone, thiacloprid, triflumezopyrim, nitenpyram, sulfoxaflor;
  - GABA antagonist compounds selected from: fipronil, ethiprole, vaniliprole, pyrafluprole, pyriprole, 5-amino-1-(2,6-dichloro-4-methyl-phenyl)-4-sulfinamoyl-1H-pyrazole-3-carbothioic acid amide;
  - ryanodine receptor inhibitors selected from: chlorantraniliprole, cyantraniliprole, and flubendiamide;

more preferably said mixtures comprise as component 1) *B. amyloliquefaciens* AP-188.

Preference is also given to mixtures comprising as component 2) at least one pesticide II from pyraclostrobin, azoxystrobin, trifloxystobin; fluxapyroxad, penflufen, sedaxane, fluopyram; ipconazole; oxathiapiprolin, valifenalate; fipronil; imidacloprid; chlorantraniliprole; and cyantraniliprole.

Particular preference is also given to mixtures comprising as component 1) *B. amyloliquefaciens* AP-188 and as component 2) at least one pesticide II from pyraclostrobin, azoxystrobin, trifloxystobin; fluxapyroxad, penflufen, sedaxane, fluopyram; ipconazole; oxathiapiprolin, valifenalate; fipronil; imidacloprid; chlorantraniliprole; and cyantraniliprole.

The inventive mixtures comprising at least one microorganism I and/or as pesticide II a microbial pesticide from groups L1), L3) and L5) may be formulated as an inoculant for a plant. The term "inoculant" means a preparation that includes an isolated culture of a microbial pesticide and optionally a carrier, which may include a biologically acceptable medium.

Herein, microbial pesticides may be supplied in any physiological state such as active or dormant. Dormant microbial pesticides may be supplied for example frozen, dried, or lyophilized or partly desiccated (procedures to produce partly desiccated organisms are given in WO 2008/002371) or in form of spores.

Microbial pesticides II selected from groups L1), L3) and L5) and the at least one microorganism I used as organisms in an active state can be delivered in a growth medium without any additional additives or materials or in combination with suitable nutrient mixtures.

The at least one microorganism I is preferably delivered and formulated in a dormant stage, more preferably in form of spores.

The mixtures and compositions according to the invention are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The mixtures and compositions according to the invention are particularly important in the control of a multitude of phytopathogenic fungi on various cultivated plants; and on the plant propagation material, such as seeds, and the crop material of these plants.

Preferably the inventive mixtures and compositions are used for controlling a multitude of fungi on the following cultivated plants: field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil.

Preferably, treatment of plant propagation materials with the inventive mixtures and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant.

The inventive mixtures and compositions are particularly suitable for controlling the following plant diseases:

*Albugo* spp. (white rust) on ornamentals, vegetables (e. g. *A. candida*) and sunflowers (e. g. *A. tragopogonis*); *Alternana* spp. (Alternaria leaf spot) on vegetables, rape (*A. brassicola* or *A. brassicae*), sugar beets (*A. tenuis*), fruits, rice, soybeans, potatoes (e. g. *A. solani* or *A. altemata*), tomatoes (e. g. *A. solani* or *A. altemata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.) on corn (e. g. *D. maydis*), cereals (e. g. *B. sorokiniana*: spot blotch), rice (e. g. *B. oryzae*) and turfs; *Blumeria* (formerly *Erysiphe*) *graminis* (powdery mildew) on cereals (e. g. on wheat or barley); *Botrytis cinerea* (teleomorph: *Botrifotinia fuckeliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn, rice, sugar beets (e. g. *C. beticola*), sugar cane, vegetables, coffee, soybeans (e. g. *C. sojina* or *C. kikuchii*) and rice; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola*), soft fruits, potatoes (e. g. *C. coccodes* black dot), beans (e. g. *C. lindemuthianum*) and soybeans (e. g. *C. truncatum* or *C. gloeosporioides*); *Corticium* spp., e. g. *C. sasakii* (sheath blight) on rice; *Corynespora cassiicola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri*: Black Foot Disease) and ornamentals; Dematophora (teleomorph: *Rosellinia*) necatrix (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis*: tan spot), rice and turf; Esca (dieback, apoplexy) on vines, caused by *Formitipona* (syn. *Phellinus*) *punctata*, *F. mediterranea*, *Phaeomoniella chlamydospora* (earlier *Phaeoacremonium chlamydosporum*), *Phaeoacremonium aleophllum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, rape (e. g. *E. cruciferarum*); *Eutypa lata* (Eutypa canker or dieback, anamorph: *Cytosporina lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* on soybeans and *F. verticillioides* on corn; *Gaeumannomyces graminis* (take-all) on cereals (e. g. wheat or barley) and corn; *Gibberella* spp. on cereals (e. g. *G. zeae*) and rice (e. g. *G. fujikuroi*: Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hemileia* spp., e. g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monilinia* spp., e. g. *M. laxa*, *M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritici*, Septoria blotch) on wheat; *Peronospora* spp. (downy mildew) on cabbage (e. g. *P. brassicae*), rape (e. g. *P. parasitica*), onions (e. g. *P. destructor*), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseoli*, teleomorph: *Diaporthe phaseolorum*); *Physoderma maydis* (brown spots) on corn; *Phytophthora* spp. (wilt, root, leaf, fruit and stem rot) on various plants, such as paprika and cucurbits (e. g. *P. capsici*), soybeans (e. g. *P. megasperma*, syn. *P. sojae*), potatoes and tomatoes (e. g. *P. infestans*: late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, and asparagus (e. g. *P. asparagi*); *Pyrenophora* (anamorph: *Drechslera*) *tritici-repentis* (tan spot) on wheat or *P. teres* (net blotch) on barley; *Pyricularia* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphani-dermatum*); *Ramularia* spp., e. g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici* (*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setospaeria* spp. (leaf blight) on corn (e. g. *S. turcicum*, syn. *Helminthosporium turcicum*) and turf; *Sphacelotheca* spp. (smut) on corn, (e. g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries*, wheat bunt) and *T. controversa* (dwarf bunt) on wheat; *Typhula incamata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseoli*) and sugar beets (e. g. *U. betae*); *Ustilago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahliae* on strawberries, rape, potatoes and tomatoes.

The mixtures and compositions according to the invention are also suitable as bactericides. They are distinguished by an outstanding effectiveness against a broad spectrum of phytopathogenic bacteria, including soil-borne bacteria, which derive especially from the genera of *Agrobacterium*, *Clavibacter*, *Corynebacterium*, *Erwinia*, *Leifsonia*, *Pectobacterium*, *Pseudomonas*, *Ralstonia*, *Xanthomonas* (e.g. *Xanthomonas oryzae* causing bacterial blight on rice) and *Xylella*; preferably *Erwinia*; even more preferably *Erwinia amylovora* causing fire blight on apples, pears and other member of the family Rosaceae.

The mixtures according to the present invention and compositions thereof, respectively, are also suitable for controlling harmful fungi in the protection of stored products or harvest.

The mixtures and compositions according to the invention are particularly important in the control of a multitude of phytopathogenic insects or other pests (e.g. lepidopterans, beetles, dipterans, *thrips*, heteropterans, hemiptera, homoptera, termites, orthopterans, arachnids, and nematodes) on various cultivated plants.

Preferably the inventive mixtures and compositions are used for controlling a multitude of pests on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The inventive mixtures and the compositions thereof, respectively, are particularly suitable for controlling the following harmful insects from the order of the lepidopterans (Lepidoptera), for example *Agrotis ypsilon*, *Agrotis segetum*, *Alabama argillacea*, *Anticarsia gemmatalis*, *Argyresthia conjugella*, *Autographa gamma*, *Bupalus piniarius*, *Cacoecia murinana*, *Capua reticulana*, *Cheimatobia brumata*, *Choristoneura fumiferana*, *Choristoneura occidentalis*, *Cirphis unipuncta*, *Cydia pomonella*, *Dendrolimus pini*, *Diaphania nitidalis*, *Diatraea grandiosella*, *Earias insulana*, *Elasmopalpus lignosellus*, *Eupoecilia ambiguella*, *Evetria bouliana*, *Feltia subterranea*, *Galleria mellonella*, *Grapholitha funebrana*, *Grapholitha molesta*, *Heliothis armigera*, *Heliothis virescens*, *Heliothis zea*, *Hellula undalis*, *Hibernia defoliaria*, *Hyphantria cunea*, *Hyponomeuta malinellus*, *Keiferia lycopersicella*, *Lambdina fiscellaria*, *Laphygma exigua*, *Leucoptera coffeella*, *Leucoptera scitella*, *Lithocolletis blancardella*, *Lobesia botrana*, *Loxostege sticticalis*, *Lymantria dispar*, *Lymantria monacha*, *Lyonetia clerkella*, *Malacosoma neustria*, *Mamestra brassicae*, *Orgyia pseudotsugata*, *Ostrinia nubilalis*, *Panoils flammea*, *Pectinophora gossypiella*, *Peridroma saucia*, *Phalera bucephala*, *Phthorimaea operculella*, *Phyllocnistis citrella*, *Pieris brassicae*, *Plathypena scabra*, *Plutella xylostella*, *Pseudoplusia includens*, *Rhyacionia frustrana*, *Scrobipalpula absoluta*, *Sitotroga cerealella*, *Sparganothis pilleriana*, *Spodoptera frugiperda*, *Spodoptera littoralis*, *Spodoptera litura*, *Thaumatopoea pityocampa*, *Tortrix viridana*, *Trichoplusia ni* and *Zeiraphera canadensis*, beetles (Coleoptera), for example *Agrilus sinuatus*, *Agriotes lineatus*, *Agriotes obscurus*, *Amphimallus solstitialis*, *Anisandrus dispar*, *Anthonomus grandis*, *Anthonomus pomorum*, *Atomaria linearis*, *Blastophagus piniperda*, *Blitophaga undata*, *Bruchus rufimanus*, *Bruchus pisorum*, *Bruchus lentis*, *Byctiscus betulae*, *Cassida nebulosa*, *Cerotoma trifurcata*, *Ceuthorrhynchus assimilis*, *Ceuthorrhynchus napi*, *Chaetocnema tibialis*, *Conoderus vespertinus*, *Crioceris asparagi*, *Diabrotica longicornis*, *Diabrotica speciosa*, *Diabrotica 12-punctata*, *Diabrotica virgifera*, *Diloboderus abderus*, *Epilachna varivestis*, *Epitrix hirtipennis*, *Eutinobothrus brasiliensis*, *Hylobius abietis*, *Hypera brunneipennis*, *Hypera postica*, *Ips typographus*, *Lema bilineata*, *Lema melanopus*, *Leptinotarsa decemlineata*, *Limonius californicus*, *Lissorhoptrus olyzophilus*, *Melanotus communis*, *Meligethes aeneus*, *Melolontha hippocastani*, *Melolontha melolontha*, *Oulema oryzae*, *Ortiorrhynchus sulcatus*, *Oryzophagus oryzae*, *Otiorrhynchus ovatus*, *Phaedon cochleariae*, *Phyllotreta chrysocephala*, *Phyllophaga* sp., *Phyl-*

*lophaga cuyabana, Phyllophaga triticophaga, Phyllopertha horticola, Phyllotreta nemorum, Phyllotreta striolata, Popillia japonica, Sitona lineatus* and *Sitophilus granaria*, dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, HaplodiplosIS equestris, Hylemyia platura, Hypoderma lineata, Liriomyza sativae, Liriomyza trifolil, Lucilia caprin, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa*, thrips (Thysanoptera), e.g. *Frankliniella fusca, Frankliniella occidentalis, Frankliniella tritici, Scirtothrips citri, Thrips oryzae, Thrips palmi* and *Thrips tabaci*, hymenopterans (Hymenoptera), e.g. *Acromyrmex ambuguus, Acromyrmex crassispinus, Acromyrmex heiery, Acromyrmex landolti, Acromyrmex subterraneus, Athalia rosae, Atta capiguara, Atta cephalotes, Atta laevigata, Atta robusta, Atta sexdens, Atta texana, Hoplocampa minuta, Hoplocampa testudinea, Monomorium pharaonic, Solenopsis geminata* and *Solenopsis invicta*, heteropterans (Heteroptera), e.g. *Acrosternum Mare, Blissus leucopterus, Cyrtopeltis notatus, Dichelops furcatus, Dysdercus cingulatus, Dysdercus intermedius, Euchistos heros, Eurygaster integriceps, Euschistus impictiventris, Leptoglossus phyllopus, Lygus lineolaris, Lygus pratensis, Nezara viridula, Piesma quadrata, Piezodorus gulldim, Solubea insularis* and *Thyanta perditor*, Hemiptera and Homoptera, e.g. *Acrosternum Mare, Blissus leucopterus, Cyrtopeltis notatus, Diaphorina citri, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphic plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hempterus, Reduvius senilis, Triatoma* spp., and *Arilus critatus*, termites (Isoptera), e.g. *Calotermes flavicollis, Cornitermes cumulans, Heterotermes tenuis, Leucotermes flavipes, Neocapritemes opacus, Procornitermes triacifer; Reticulitermes lucifugus, Syntermes molestus,* and *Termes natalensis*, orthopterans (Orthoptera), e.g. *Acheta domestica, Blatta orientalis, Blattella germanica, Forticula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus*, Arachnoidea, such as arachnids, e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis*.

In particular, the inventive mixtures are suitable for combating pests of the orders Coleoptera, Lepidoptera, Thysanoptera, Homoptera, Isoptera, and Orthoptera.

They are also suitable for controlling the following plant parasitic nematodes such as root-knot nematodes, *Meloidogyne arenaria, Meloidogyne chitwoodi, Meloidogyne exigua, Meloidogyne hapla, Meloidogyne incognita, Meloidogyne javanica* and other *Meloidogyne* species; cyst nematodes, *Globodera rostochiensis, Globodera pallida, Globodera tabacum* and other *Globodera* species, *Heterodera avenae, Heterodera glycines, Heterodera schachtii, Heterodera trifolii* and other *Heterodera* species; seed gall nematodes, *Anguina funesta, Anguina tritici* and other *Anguina* species; stem and foliar nematodes, *Aphelenchoides besseyi, Aphelenchoides fragariae, Aphelenchoides ritzemabosi* and other *Aphelenchoides* species; sting nematodes, *Belonolaimus longicaudatus* and other *Belonolaimus* species; pine nematodes, *Bursaphelenchus xylophilus* and other *Bursaphelenchus* species; ring nematodes, *Criconema* species, *Criconemella* species, *Criconemoides* species, and *Mesocriconema* species; stem and bulb nematodes, *Ditylenchus destructor, Ditylenchus dipsaci, Ditylenchus myceliophagus* and other *Ditylenchus* species; awl nematodes, *Dolichodorus* species; spiral nematodes, *Helicotylenchus dihystera, Helicotylenchus multicinctus* and other *Helicotylenchus* species, *Rotylenchus robustus* and other *Rotylenchus* species; sheath nematodes, *Hemicycliophora* species and *Hemicriconemoides* species; *Hirshmanniella* species; lance nematodes, *Hoplolaimus columbus, Hoplolaimus galeatus* and other *Hoplolaimus* species; false root-knot nematodes, *Nacobbus aberrans* and other *Nacobbus* species; needle nematodes, *Longidorus elongates* and other *Longidorus* species; pin nematodes, *Paratylenchus* species; lesion nematodes, *Pratylenchus brachyurus, Pratylenchus coffeae, Pratylenchus curvitatus, Pratylenchus goodeyi, Pratylencus neglectus, Pratylenchus penetrans, Pratylenchus scribneri, Pratylenchus vulnus, Pratylenchus zeae* and other *Pratylenchus* species; *Radinaphelenchus cocophilus* and other *Radinaphelenchus* species, burrowing nematodes, *Radopholus similis* and other *Radopholus* species; reniform nematodes, *Rotylenchulus reniformis* and other *Rotylenchulus* species; *Scutellonema* species; stubby root nematodes, *Trichodorus primitivus* and other *Trichodorus* species; *Paratrichodorus minor* and other *Paratrichodorus* species, stunt nematodes, *Tylenchorhynchus claytoni, Tylenchorhynchus dubius* and other *Tylenchorhynchus* species and *Merlinius* species; citrus nematodes, *Tylenchulus semipenetrans* and other *Tylenchulus* species; dagger nematodes, *Xiphinema americanum, Xiphinema index, Xiphinema diversicaudatum* and other *Xiphinema* species; and other plant parasitic nematode species Plant propagation materials may be treated with the mixtures and compositions of the invention prophylactically either at or before planting or transplanting.

In particular, the present invention relates to a method for protection of plant propagation material from pests, wherein the plant propagation material is treated with an effective amount of an inventive mixture.

In a preferred embodiment, the present invention relates to a method for protection of plant propagation material from animal pests (insects, acarids or nematodes), wherein the plant propagation material are treated with an effective amount of an inventive mixture.

In an equally preferred embodiment, the present invention relates to a method for protection of plant propagation material from harmful fungi, wherein the plant propagation material is treated with an effective amount of an inventive mixture.

For example, for seed treatment and soil applications, it is evident that a plant suffering from fungal or insecticidal attack shows reduced germination and emergence leading to poorer plant or crop establishment and vigor, and consequently, to a reduced yield as compared to a plant propagation material which has been subjected to curative or preventive treatment against the relevant pest and which can grow without the damage caused by the biotic stress factor. However, the methods according to the invention lead to an enhanced plant health even in the absence of any biotic stress. This means that the positive effects of the mixtures of the invention cannot be explained just by the pesticidal activities of microorganisms I and pesticides II, but are based on further activity profiles. Accordingly, the application of the inventive mixtures can also be carried out in the absence of pest pressure.

The term "plant health" is to be understood to denote a condition of the plant and/or its products which is determined by several indicators alone or in combination with each other such as yield (e. g. increased biomass and/or increased content of valuable ingredients), plant vigor (e. g. improved plant growth and/or greener leaves ("greening effect")), quality (e. g. improved content or composition of certain ingredients) and tolerance to abiotic and/or biotic stress.The above identified indicators for the health condition of a plant may be interdependent, or may result from each other.

In an equally preferred embodiment, the present invention relates to a method for improving the health of plants grown from said plant propagation material, wherein the plant propagation material is treated with an effective amount of an inventive mixture.

In an equally preferred embodiment, the present invention relates to a method for improving the health of plants, wherein the plant is treated with an effective amount of an inventive mixture.

Each plant health indicator such as yield, plant vigor, quality and tolerance of the plant to abiotic and/or biotic stress, is to be understood as a preferred embodiment of the present invention either each on its own.

The invention also relates to agrochemical compositions comprising an auxiliary and at least one microorganism I, or a cell-free extract thereof or at least one metabolite thereof having pesticidal activity, and/or a mutant of a microorganism I having pesticidal activity and producing at least one pesticidal metabolite as defined herein, or a pesticidal metabolite or extract of the mutant, and at least one pesticide II according to the invention.

An agrochemical composition comprises a fungicidally or insecticidally effective amount of at least one microorganism I and at least one pesticide II. Such an amount can vary in a broad range and is dependent on various factors, such as the fungal or pest species to be controlled, the treated cultivated plant or material, the climatic conditions.

In the case of mixtures comprising microbial pesticides II selected from groups L1), L3) and L5), the microorganisms as used according to the invention can be cultivated continuously or discontinuously in the batch process or in the fed batch or repeated fed batch process. A review of known methods of cultivation will be found in the textbook by Chmiel (Bioprozesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)). The culture medium that is to be used must satisfy the requirements of the particular strains in an appropriate manner. Descriptions of culture media for various microorganisms are given in the handbook "Manual of Methods for General Bacteriology" of the American Society for Bacteriology (Washington D. C., USA, 1981). Information on media optimization can be found in the textbook "Applied Microbiol. Physiology, A Practical Approach" (Publ. P. M. Rhodes, P. F. Stanbury, IRL Press (1997) p. 53-73, ISBN 0 19 963577 3).

According to one embodiment, individual components of the composition according to the invention such as parts of a kit or parts of a binary or ternary mixture may be mixed by the user himself in a spray tank or any other kind of vessel used for applications (e.g seed treater drums, seed pelleting machinery, knapsack sprayer) and further auxiliaries may be added, if appropriate. When living microorganisms, such as microorganisms I and pesticides II from groups L1), L3) and L5), form part of such kit, it must be taken care that choice and amounts of the other parts of the kit (e.g. chemcial pesticidal agents) and of the further auxiliaries should not influence the viability of the microbial pesticides in the composition mixed by the user. Especially for bactericides and solvents, compatibility with the respective microbial pesticide has to be taken into account.

Consequently, one embodiment of the invention is a kit for preparing a usable pesticidal composition, the kit compring a) a composition comprising component 1) as defined herein and at least one auxiliary; and b) a composition comprising component 2) as defined herein and at least one auxiliary.

The at least one pesticide II can be converted into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6$^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

When living microorganisms, such as microorganisms I and pesticides II from groups L1), L3) and L5), form part of the compositions, such compositions can be prepared as compositions comprising besides the active ingredients at least one auxiliary (inert ingredient) by usual means (see e.g. H. D. Burges: Formulation of Micobial Biopesticides, Springer, 1998). Suitable customary types of such compositions are suspensions, dusts, powders, pastes, granules, pressings, capsules, and mixtures thereof. Examples for composition types are suspensions (e.g. SC, OD, FS), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). Herein, it has to be taken into account that each formulation type or choice of auxiliary should not influence the viability of the microorganism during storage of the-composition and when finally applied to the soil, plant or plant propagation material. Suitable formulations are e.g. mentioned in WO 2008/002371, U.S. Pat. No. 6,955,912, U.S. Pat. No. 5,422,107.

Examples for suitable auxiliaries are those mentioned earlier herein, wherein it must be taken care that choice and amounts of such auxiliaries should not influence the viability of the microbial pesticides in the composition. Especially for bactericides and solvents, compatibility with the respective microorganism of the respective microbial pesticide has to be taken into account. In addition, compositions with microbial pesticides may further contain stabilizers or nutrients and UV protectants. Suitable stabilzers or nutrients are e.g. alpha-tocopherol, trehalose, glutamate, potassium sorbate, various sugars like glucose, sucrose, lactose and maltodextrine (H. D. Burges: Formulation of Micobial Biopesticides, Springer, 1998). Suitable UV protectants are e.g. inorganic compouns like titan dioxide, zinc oxide and iron oxide pigments or organic compounds like benzophenones, benzotriazoles and phenyltriazines. The compositions may in addition to auxiliaries mentioned for compositions comprising compounds I herein optionally comprise 0.1-80% stabilizers or nutrients and 0.1-10% UV protectants.

The agrochemical compositions generally are characterized in that they contain an effective quantity of the active components as defined above. Generally, they contain between 0.01 and 95%, preferably between 0.1 and 90%, and in particular between 0.5 and 75%, by weight of active components, in particular active substances.

According to one embodiment, the compositions contain microbial pesticides such as TJ1000 and pesticides II from groups L1), L3) and L5) in an amount from $1\times10^5$ to $1\times10^{12}$ CFU, preferably from $1\times10^7$ CFU to $1\times10^{12}$ CFU, more preferably from $1\times10^9$ CFU to $1\times10^{12}$ CFU per gram total weight of the composition.

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds.

Preferred examples of seed treatment formulation types or soil application for pre-mix compositions are of WS, LS, ES, FS, WG or CS-type.

The compositions in question give, after two-to-tenfold dilution, active components concentrations of from 0.01 to 60% by weight, preferably from 0.1 to 40%, in the ready-to-use preparations. Application can be carried out before or during sowing. Methods for applying or treating compound I and compound II and compositions thereof, respectively, on to plant propagation material, especially seeds include dressing, coating, pelleting, dusting, soaking and in-furrow application methods of the propagation material. Preferably, compound I and compound II or the compositions thereof, respectively, are applied on to the plant propagation material by a method such that germination is not induced, e. g. by seed dressing, pelleting, coating and dusting.

It is preferred that the plant propagation material is a seed, seed piece (i.e. stalk) or seed bulb.

Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications). The seed may also be primed either before or after the treatment.

Even distribution of the ingredients in inventive mixtures and adherence thereof to the seeds is desired during propagation material treatment. Treatment could vary from a thin film (dressing) of the formulation containing the combination, for example, a mixture of active ingredient(s), on a plant propagation material, such as a seed, where the original size and/or shape are recognizable to an intermediary state (such as a coating) and then to a thicker film (such as pelleting with many layers of different materials (such as carriers, for example, clays; different formulations, such as of other active ingredients; polymers; and colourants) where the original shape and/or size of the seed is no longer recognizable.

Seed can be treated by applying thereto the component 1) and component 2) present in the inventive mixtures in any desired sequence or simultaneously.

The seed treatment occurs to an unsown seed, and the term "unsown seed" is meant to include seed at any period between the harvest of the seed and the sowing of the seed in the ground for the purpose of germination and growth of the plant. Treatment to an unsown seed is not meant to include those practices in which the active ingredient is applied to the soil but would include any application practice that would target the seed during the planting process.

Preferably, the treatment occurs before sowing of the seed so that the sown seed has been pre-treated with the combination. In particular, seed coating or seed pelleting are preferred in the treatment of the combinations according to the invention. As a result of the treatment, the ingredients in each combination are adhered on to the seed and therefore available for pest control.

The treated seeds can be stored, handled, sowed and tilled in the same manner as any other active ingredient treated seed.

In particular, the present invention relates to a method for protection of plant propagation material from pests and/or improving the health of plants grown from said plant propagation material, wherein the soil, wherein plant propagation material is sown, is treated with an effective amount of an inventive mixture.

In particular, the present invention relates to a method for protection of plant propagation material from pests, wherein the soil, wherein plant propagation material is sown, is treated with an effective amount of an inventive mixture.

In particular, the present invention relates to a method for protection of plant propagation material from harmful fungi, wherein the soil, wherein plant propagation material is sown, is treated with an effective amount of an inventive mixture.

In particular, the present invention relates to a method for protection of plant propagation material from animal pests (insects, acarids or nematodes), wherein the soil, wherein plant propagation material is sown, is treated with an effective amount of an inventive mixture.

When employed in plant protection, the total amounts of active components applied are, depending on the kind of effect desired, from 0.001 to 10 kg per ha, preferably from 0.005 to 2 kg per ha, more preferably from 0.05 to 0.9 kg per ha, in particular from 0.1 to 0.75 kg per ha. In the case of microorganisms I and microbial pesticides II, the application rates for foliar or soil (e. g. in furrow) application methods preferably range from about $1 \times 10^6$ to $5 \times 10^{15}$ (or more) CFU/ha and even more preferably, the spore concentration is about $1 \times 10^7$ to about $1 \times 10^{12}$ CFU/ha.

When employed in plant protection by seed treatment, the amount of the inventive mixtures (based on total weight of active components) is in the range from 0.01-10 kg, preferably from 0.1-1000 g, more preferably from 1-100 g per 100 kilogram of plant propagation material (preferably seeds). In the case of microorganisms I and microbial pesticides II, the application rates with respect to plant propagation material preferably range from about $1 \times 10^6$ to $1 \times 10^{12}$ (or more) CFU/seed. Preferably, the concentration is about $1 \times 10^6$ to about $1 \times 10^{11}$ CFU/seed. In the case of microorganisms I and microbial pesticides II, the application rates with respect to plant propagation material also preferably range from about $1 \times 10^7$ to $1 \times 10^{14}$ (or more) CFU per 100 kg of seed, preferably from $1 \times 10^9$ to about $1 \times 10^{11}$ CFU per 100 kg of seed.

When used in the protection of materials or stored products, the amount of active components applied depends on the kind of application area and on the desired effect. Amounts customarily applied in the protection of materials are 0.001 g to 2 kg, preferably 0.005 g to 1 kg, of active components per cubic meter of treated material.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

In the mixtures and compositions, the compound ratios are advantageously chosen so as to produce a synergistic effect.

The term "synergstic effect" is understood to refer in particular to that defined by Colby's formula (Colby, S. R., "Calculating synergistic and antagonistic responses of herbicide combinations", Weeds, 15, pp. 20-22, 1967).

The term "synergistic effect" is also understood to refer to that defined by application of the Tammes method, (Tammes, P. M. L., "Isoboles, a graphic representation of synergism in pesticides", Netherl. J. Plant Pathol. 70, 1964).

According to the invention, the solid material (dry matter) of the biopesticides (with the exception of oils such as Neem oil, Tagetes oil, etc.) are considered as active components (e.g. to be obtained after drying or evaporation of the extraction medium or filtration of the suspension medium in case of liquid formulations of the microbial pesticides).

In accordance with the present invention, the weight ratios and percentages used herein for a biological extract such as Quillay extract are based on the total weight of the dry content (solid material) of the respective extract(s).

The total weight ratios of compositions comprising at least one microbial pesticide in the form of viable microbial cells including dormant forms, can be determined using the amount of CFU of the respective microorganism to calculate the total weight of the respective active component with the following equation that $1 \times 10^{10}$ CFU equals one gram of total weight of the respective active component. Colony forming unit is a measure of viable microbial cells, in particular fungal and bacterial cells. In addition, here "CFU" may also be understood as the number of (juvenile) individual nematodes in case of (entomopathogenic) nematode biopesticides, such as *Steinernema feltiae*.

In the mixtures and compositions according to the invention the weight ratio of the component 1) and the component 2) generally depends from the properties of the active components used, usually it is in the range of from 1:10,000 to 10,000:1, regularly in the range of from 1:100 to 10,000:1, preferably in the range of from 1:100 to 5,000:1, more preferably in the range of from 1:1 to 1,000:1, even more preferably in the range of from 1:1 to 500:1 and in particular in the range of from 10:1 to 300:1.

According to further embodiments of the mixtures and compositions, the weight ratio of the component 1) and the component 2) usually is in the range of from 20,000:1 to 1:10, often in the range of from 10,000:1 to 1:1, regularly in the range of from 5,000:1 to 5:1, preferably in the range of from 5,000:1 to 10:1, more preferably in the range of from 2,000:1 to 30:1, even more preferably in the range of from 2,000:1 to 100:1 and in particular in the range of from 1,000:1 to 100:1.

According to further embodiments of the mixtures and compositions, the weight ratio of the component 1) and the component 2) usually is in the range of from 20,000:1 to 1:1,000, often in the range of from 10,000:1 to 1:100, regularly in the range of from 5,000:1 to 1:1, preferably in the range of from 5,000:1 to 10:1, more preferably in the range of from 2,000:1 to 30:1, even more preferably in the range of from 2,000:1 to 100:1 and in particular in the range of from 1,000:1 to 100:1.

According to further embodiments of the mixtures and compositions, the weight ratio of the component 1) and the component 2) usually is in the range of from 1:1 to 1:1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

In the abovementioned emodiments the total weight of component 1) is calculated on the basis of of the amount of CFU of component 1), wherein $1\times10^{10}$ CFU equals one gram of total weight of component 1); and the total weight of component 2) in case of microorganisms is calculated on the basis of of the amount of CFU of component 2), wherein $1\times10^{10}$ CFU equals one gram of total weight of component 2).

These ratios are also suitable for inventive mixtures applied by seed treatment.

The fungicidal action of the mixtures according to the invention can be shown by the tests described below.

A) Microtiter Plate Tests

The chemical pesticides II were formulated separately as a stock solution having a concentration of 10000 ppm in dimethyl sulfoxide.

The stock solutions of the chemical pesticides II were mixed according to the ratio, diluted to the stated concentrations and pipetted onto a filter micro titer plate (MTP). A spore suspension of the pathogen (e.g. *Botrytis cinerea*, *Septoria tritici*, etc.) in e.g. aqueous biomalt solution was added as well as different concentrations of spores or cells of microorganisms I and, if applicable, the microbial pesticides II.

The measured parameters were compared to the growth of the active compound-free control variant (100%) and the fungus-free and active compound-free blank value to determine the relative growth in % of the pathogens in the respective active compounds.

The expected efficacies of active compound combinations were determined using Colby's formula (Colby, S. R., Calculating synergistic and antagonistic responses of herbicide combinations, Weeds, 15, pp. 20-22, 1967) and compared with the observed efficacies.

Colby's formula: $E = x + y - x \cdot y/100$

E expected efficacy, expressed in % of the untreated control, when using the mixture of the active components A and B at the concentrations a and b x efficacy, expressed in % of the untreated control, when using the active component A at the concentration a y efficacy, expressed in % of the untreated control, when using the active component B at the concentration b.

We claim:

1. A mixture comprising, as active components present in a synergistically effective amount:

1) at least one microorganism I of the genus *Bacillus* that is *B. amyloliquefaciens* AP-188 (NRRL B-50331; NRRL B-50615); and 2) at least one pesticide II selected from pyraclostrobin and fluxapyroxad.

2. The mixture of claim 1, wherein component 1) and component 2) are present in a total weight ratio of from 10,000:1 to 1:100; wherein the total weight of component 1) is calculated on the basis of the amount of CFU of component 1), wherein $1\times10^{10}$ CFU equals one gram of total weight of component 1); and wherein the total weight of component 2) in case of microorganisms is calculated on the basis of the amount of CFU of component 2), wherein $1\times10^{10}$ CFU of equals one gram of total weight of component 2).

3. The mixture of claim 1, wherein component 2) is pyraclostrobin.

4. The mixture of claim 3, wherein component 2) is fluxapyroxad.

5. An agrochemical composition comprising an auxiliary and the mixture of claim 1.

6. A method for controlling phytopathogenic fungi, insects or other pests and/or improving the health of plants and/or regulating plant growth, comprising treating the plants, the plant propagation material or the soil with an effective amount of the mixture of claim 1.

7. A method for controlling phytopathogenic fungi, insects or other pests and/or improving the health of plants and/or regulating plant growth, comprising treating the plants, the plant propagation material or the soil with an effective amount of the composition of claim 5.

8. The method of claim 7, wherein component 2) is pyraclostrobin.

9. The method of claim 7, wherein component 2) is pyraclostrobin and fluxapyroxad.

10. A plant propagation material, comprising the mixture of claim 1 in an amount of from 0.01 g to 10000 g per 100 kg of plant propagation material.

11. A plant propagation material treated with a composition comprising the mixture of claim 1 in an amount of from 0.01 g to 10000 g of the mixture per 100 kg of plant propagation material.

12. A kit for preparing a usable agrochemical composition, the kit comprising as active components:

1) at least one microorganism I of the genus *Bacillus* that is *B. amyloliquefaciens* AP-188 (NRRL B-50331; NRRL B-50615); and 2) at least one pesticide II selected from.

* * * * *